(12) United States Patent
Gilligan et al.

(10) Patent No.: US 6,319,685 B1
(45) Date of Patent: *Nov. 20, 2001

(54) ALPHA-AMIDATING ENZYME COMPOSITIONS AND PROCESSES FOR THEIR PRODUCTION AND USE

(75) Inventors: James P. Gilligan, Union; Barry N. Jones, West Milford, both of NJ (US)

(73) Assignee: Unigene Laboratories, Inc., Fairfield, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/086,161

(22) Filed: Aug. 14, 1987

Related U.S. Application Data

(63) Continuation-in-part of application No. 06/655,366, filed on Sep. 27, 1984, now Pat. No. 4,708,934.

(51) Int. Cl.$^7$ .......................... C12P 21/02; C07K 14/47; C07K 1/16; C07K 1/17
(52) U.S. Cl. ................... 435/68.1; 530/350; 530/416; 530/417
(58) Field of Search ................. 435/68, 69, 70, 435/228, 177, 181, 68.1; 935/51, 14; 530/350, 416, 417

(56) References Cited

U.S. PATENT DOCUMENTS

| | | | |
|---|---|---|---|
| 4,518,693 | * 5/1985 | Kuu et al. ................ | 435/161 X |
| 4,549,986 | 10/1985 | Evans et al. .............. | 350/307 |
| 4,708,934 | * 11/1987 | Gilligan et al. ............ | 435/68 |
| 4,921,797 | 5/1990 | Matsuo et al. ............ | 435/129 |

FOREIGN PATENT DOCUMENTS

| | | |
|---|---|---|
| 0134631 | 3/1985 | (EP) . |
| 0197794 | 10/1986 | (EP) . |
| 0249412 | 12/1987 | (EP) . |
| 0249477 | 12/1987 | (EP) . |
| 0299790 | 1/1989 | (EP) . |
| 0308067 | 3/1989 | (EP) . |
| 2141430 | 12/1984 | (GB) . |
| 62-177184 | 7/1987 | (JP) . |
| 62-306867 | 12/1987 | (JP) . |
| WO-A-8602099 | 4/1986 | (WO) . |
| WO 87/01729 | 3/1987 | (WO) . |
| WO89/02460 | 3/1989 | (WO) . |
| WO-A-9008190 | 7/1990 | (WO) . |

OTHER PUBLICATIONS

Eipper, B., et al, *Proc National Acad Sci*, vol. 80, pp. 5144–5147, 1983.*
Bradbury, A. et al, *Nature*, vol. 298, pp. 686–687, 1982.*
Kizer, J., et al, *Proc. Nat. Acad Sci*, vol. 81, pp. 3228–3233, May, 1984.*
Gomez, S. et al, *FEBS Letters*, vol. 167, pp. 160–164, Feb., 1984.*
Pharmacia Fine Chem. Catalogue, pp. 21–23, 1984.*
Gel Filtration, Theory & Practice, Pharmacia Fine Chemicals, p12–15, 1982.*
Morris et al, *Nature*, vol. 308, pp. 746–748, 1984 (Apr.).*
Gubler et al, *Proc. Natl Acad Sci*, vol. 80, pp. 4311–4314, Jul., 1983.*
Eipper, et al., Structure of the Precursor to an Enzyme . . . , (1987) Molecular Endo., vol. 1, No. 1, pp. 777–790.
Perkins, et al., (1990)Stable Expression of Full–Length and Truncated Bovine . . . , Molecular Endo., vol. 4, No. 1, pp. 132–139.
Stoffers, et al., Alternative mRNA splicing . . . , (1/89) Proc.Natl. Acad.Sci., vol. 86, No. 2, pp. 735–739.
Glauder,et al.,Human Peptidylglycine alpha–amidating . . . , Biochem.&Boiphys.Res.Comm., vol. 169, No. 2, pp. 551–558(Jun. 15, 1990).
Mizuno et al., "Peptide C–Terminal α –Amidating Enzyme Purified to Homogeneity from *Xenopus Laevis* Skin", *Biochem. Biophys. Res. Comm.*, vol. 137, No. 3 pp. 984–991 (1986).
Murthy et al., "Purification and Characterization of Peptidylglycine α –Amidating Monooxygenase from Bovine Neurointermediate Pituitary", *J. Biol. Chem.*, vol. 261, No. 4 pp. 1815–1822 (1986).
Husain, "Formation of the COOH–Terminal Amide Group of Thyrotropin–Releasing–Factor," *FEBS Letters*, vol. 152, No. 2 pp. 277–281 (1983).
Gilligan et al., "Characterization of an α –Amidating Enzyme From Rat CA–77 Cells: Its Use For the Production of Recombinent Human Calcitonin and GHRF" (1986) Miami Winter Symposium.

(List continued on next page.)

*Primary Examiner*—Robert A. Schwartzman
(74) *Attorney, Agent, or Firm*—Ostrolenk, Faber, Gerb & Soffen, LLP

(57) ABSTRACT

Purified enzymatic compositions are provided having alpha-amidating enzymes capable of catalyzing the conversion of a peptidyl compound having a C-terminal glycine residue to a corresponding peptidyl amide having an amino group in place of the C-terminal glycine. The purified compositions have specific activities above 25 mU per mg protein and are sufficiently free of proteases to allow effective catalysis of even peptidyl compounds having L-amino acids. Biologically important alpha-amidated products such as calcitonin and other regulatory hormones are efficiently produced using the alpha-amidation reaction catalyzed by the enzymes. Purification by size exclusion chromatography in combination with strong anion exchange chromatography results in homogeneous enzyme species which are used to prepare antibodies specific for the alpha-amidating enzyme. A gene capable of expressing the alpha-amidating enzyme is ligated into an expression vector and transformed into a host cell capable of expressing the gene.

19 Claims, 19 Drawing Sheets

OTHER PUBLICATIONS

Young et al., "Liberation of Salmon Calcitonin or Human Calcitonin Gene Related Peptide from Fusion Protein Using Chemical Cleavages at Aspartylprolyl and Methionyl Peptide Bonds" (1987) Abstract Submitted for First Symposium of the Protein Society Aug. 9–13.

Tamburini et al., "Purification and Characterization of Multiple Forms of Peptidyl α –Amidating Enzymes from Cultured Rat Medulary Thyroid Carcinoma (MTC) CA–77 Cells" (1987) Abstract Submitted for First Symposium of the Protein Society, Aug. 9–13.

Jones et al., "The Use of Dansylated Peptide Substrates for the Characterization of Peptadyl α –Amidating Activity" (1987) Abstract Submitted for the First Symposium of the Protein Society. Aug. 9–13.

Young et al., "Preparation, Isolation and Chemical Characterization of Recombinant Human Growth Hormone Releasing Factor" (1985) Abstract Submitted for Symposium of American Protein Chemists Sep. 30–Oct. 3, 1985.

Mehta et al., "Purification and Characterization of an Amidating Enzyme Involved in Peptide Hormone Processing" (1987) Abstract Submitted to the Endocrine Society Meeting, Indianapolis, Jun. 10–12, 1987.

Jones et al., "Preparation, Isolation and Chemical Characterization of Recombinant Human Calcitonin" (1985) Abstract Submitted for the Symposium of American Protein Chemists, Sep. 30–Oct. 3, 1985.

Glembotski et al., Characterization of a Peptide alpha–Amidation Activity from Rat Anterior Pituitary:, *J. Biol. Chem.*, Vo. 259 (10), pp. 6385–6392 (1984), *Chem Abst.* p. 244, 101:50587W.

Mains et al., Hormonal Drug and Dietary Factors Affecting Peptidyl Glycine alpha–Amidating Monooxygenase Activity in Various Tissues of the Adult Male Rat:, *Endo* vol. 116, No. 6, pp. 2505–2515 (1985).

Eipper et al., *Peptides,* Vo. 4, pp. 921–928 (1983).

Glembotski, "Further Characterization of their Peptidyl alpha–Amidating Enzyme in Rat Anterior Pituitary Secretory Granules", Arch Biochem & Biophys, vol. 241 No. 2, pp. 673–683 (1985).

Amara et al., PNAS, Vo. 77 pp. 4444–4448, (1980).

Myhre et al. *Acta Endocrin,* Vo. 99, pp. 387–403 (1982).

Hsueh et al., *Proteases, Potential Role in Health and Diseases,* Plenum Press, New York and London, pp. 141–151 (1984).

Pharmacia Fine Chemicals Catalogue, 1984, p. 9.

* cited by examiner

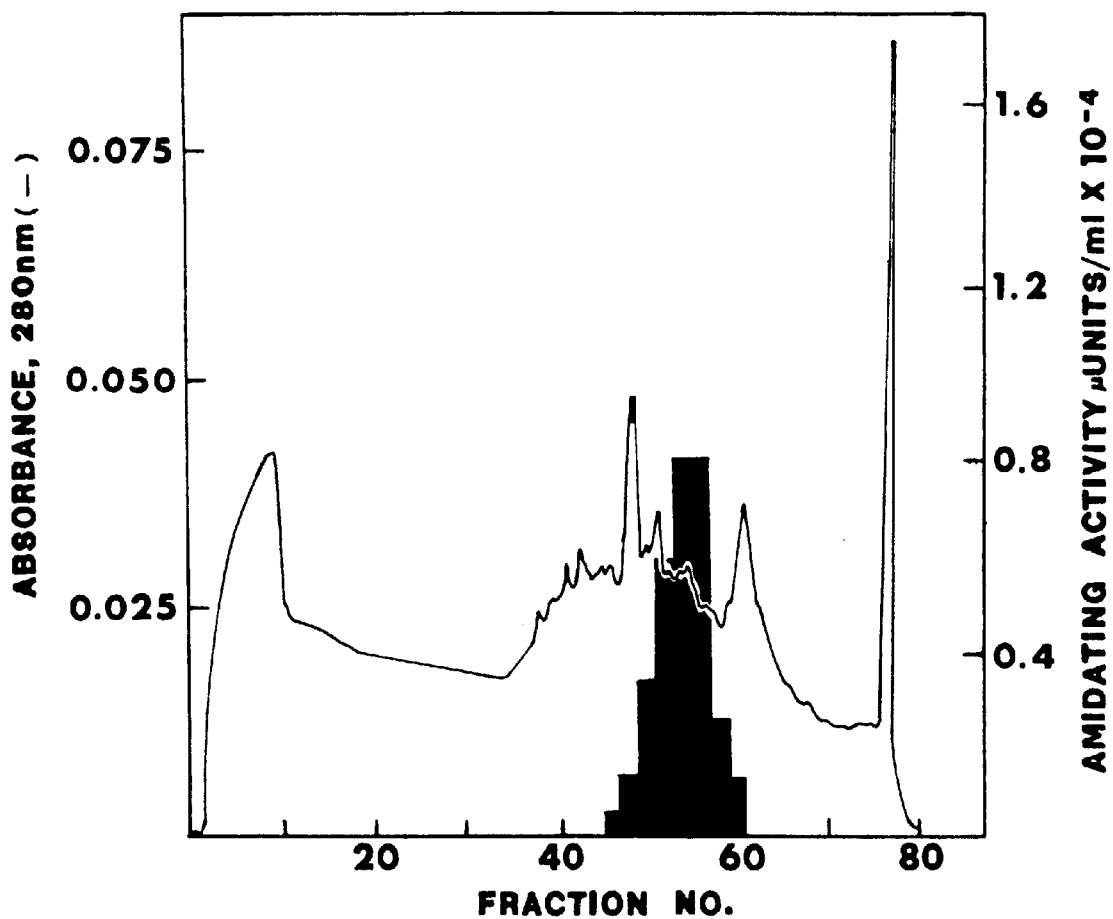
FIG. II.

FIG. III
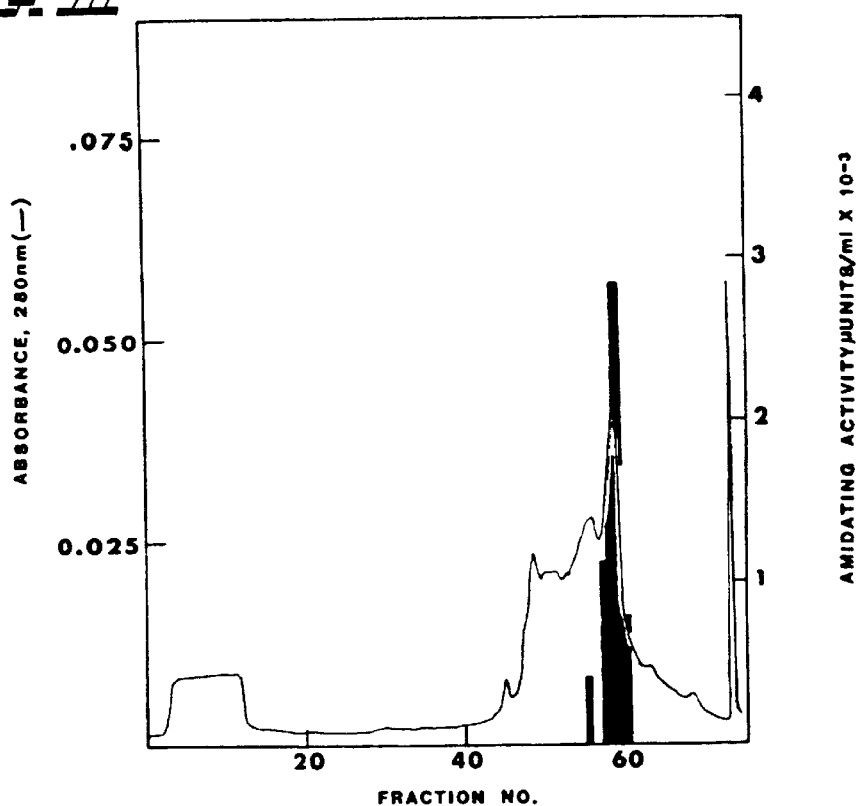
FIG. IV
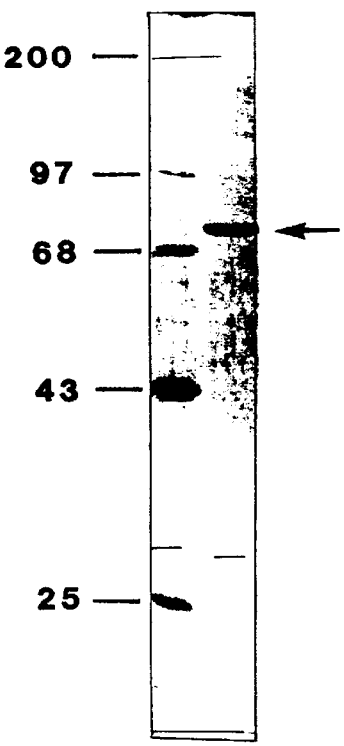

_FIG. V._
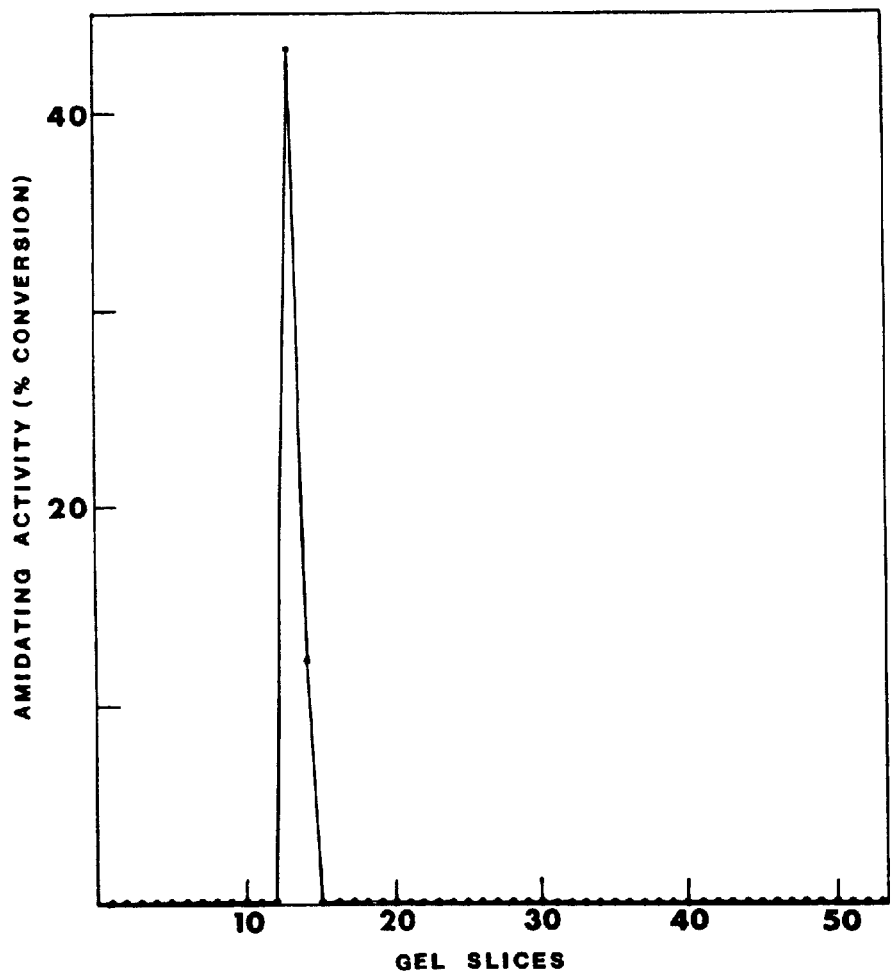
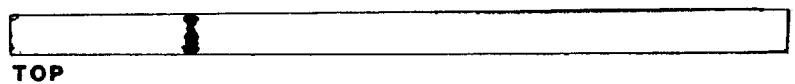
_FIG. VI._
DESIGN OF FUSION PROTEIN GENE

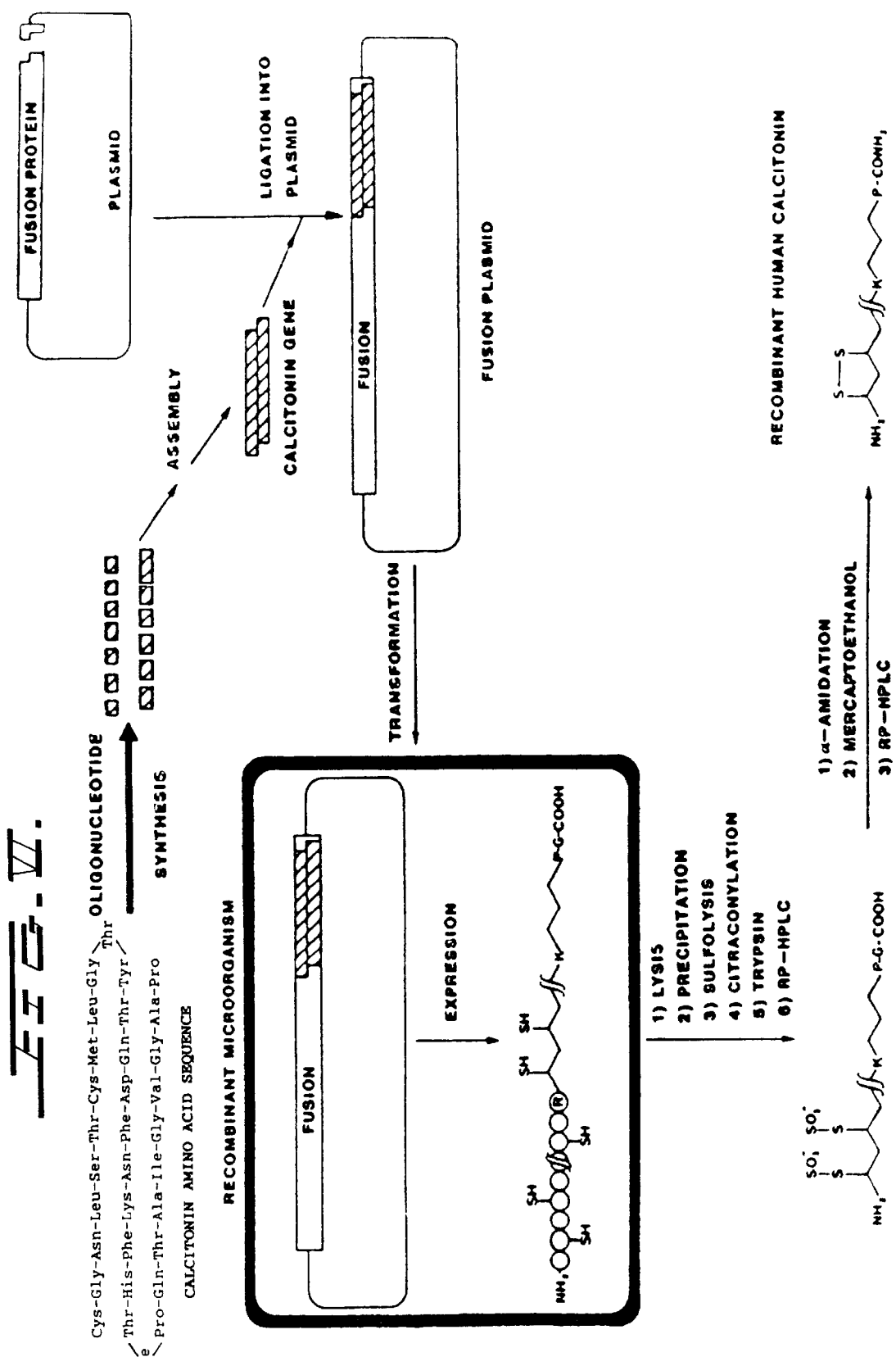

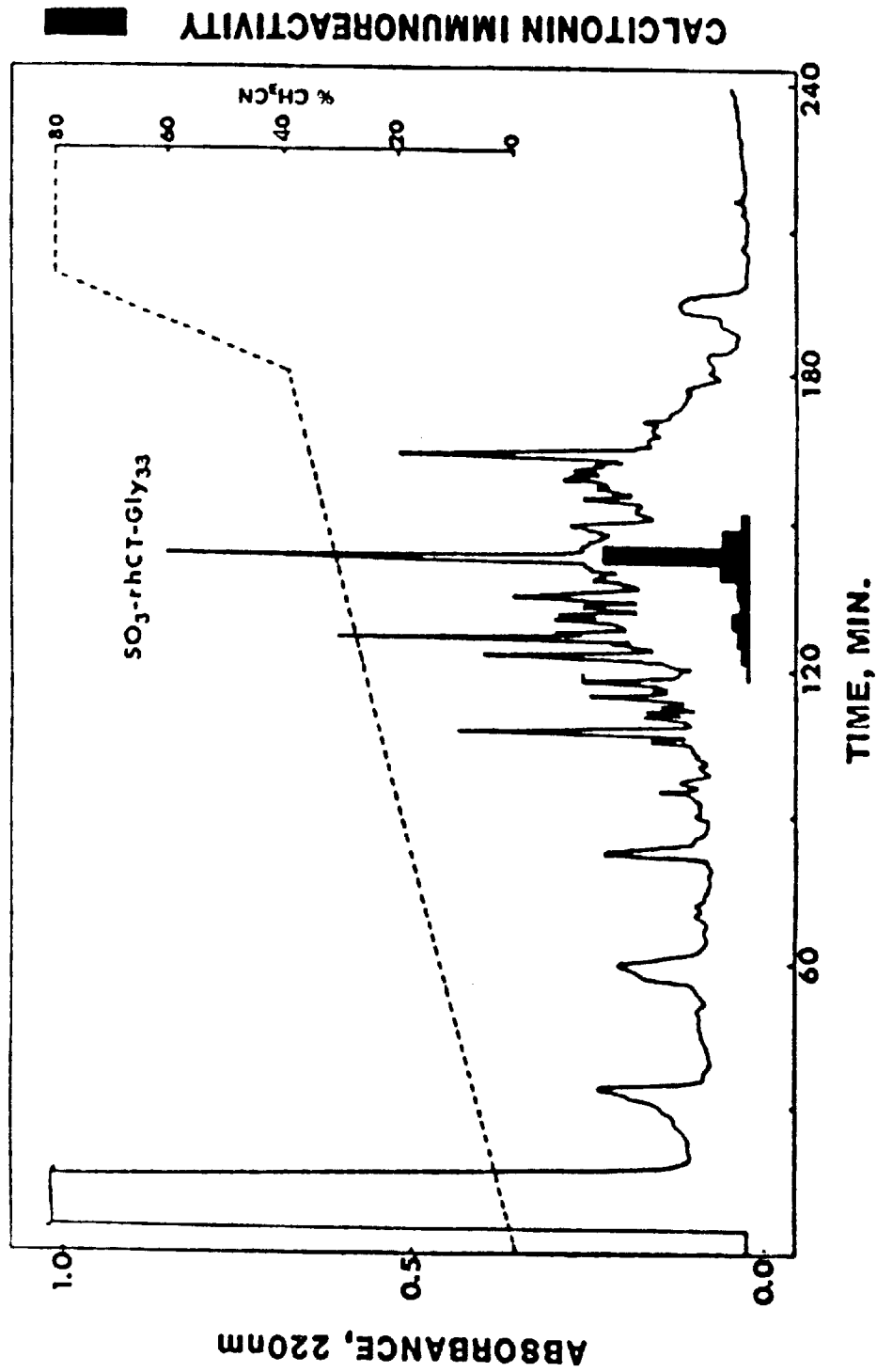
FIG. VII. RP-HPLC: TRYPTIC DIGEST OF FUSION PROTEIN

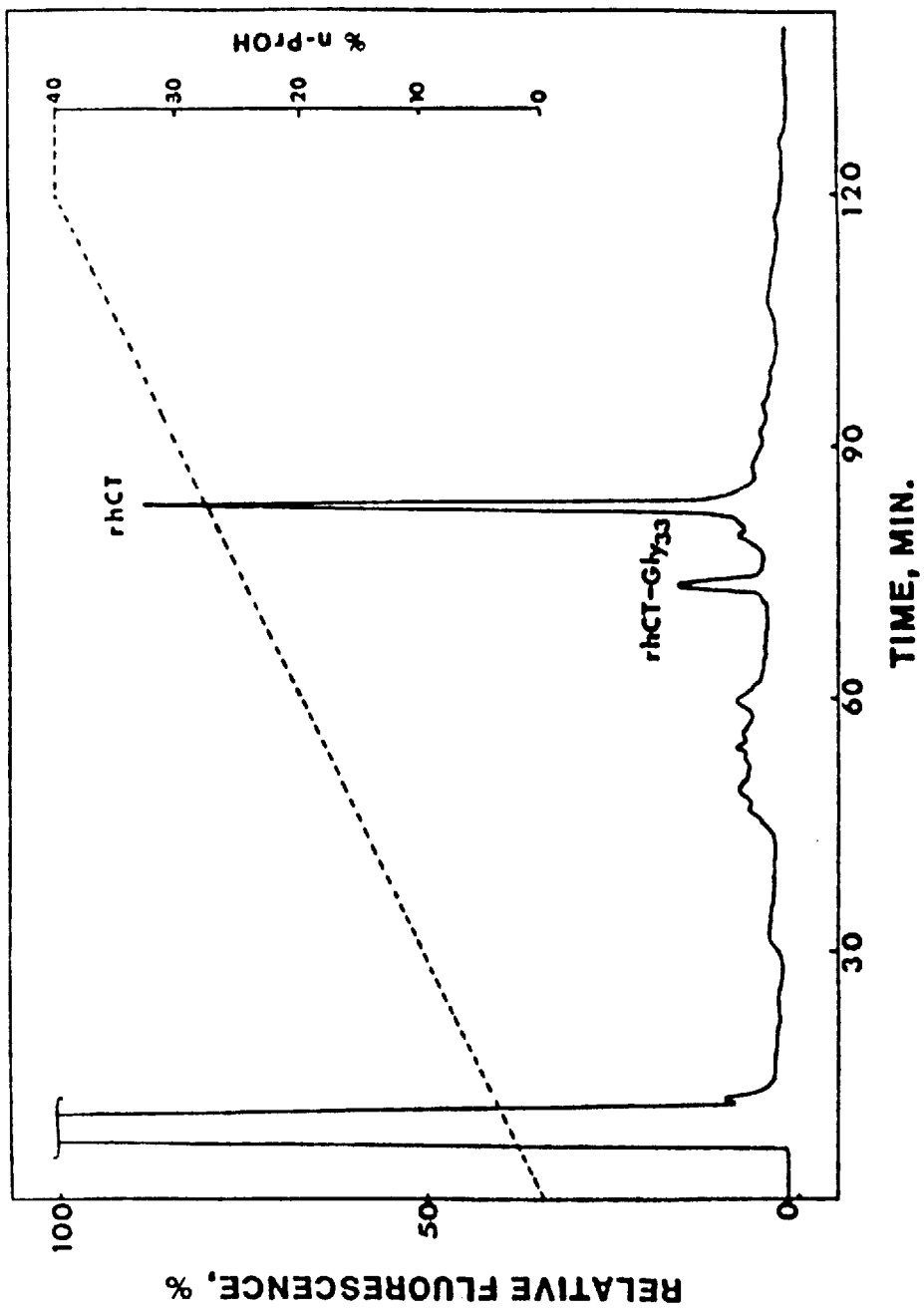
FIG. IX.

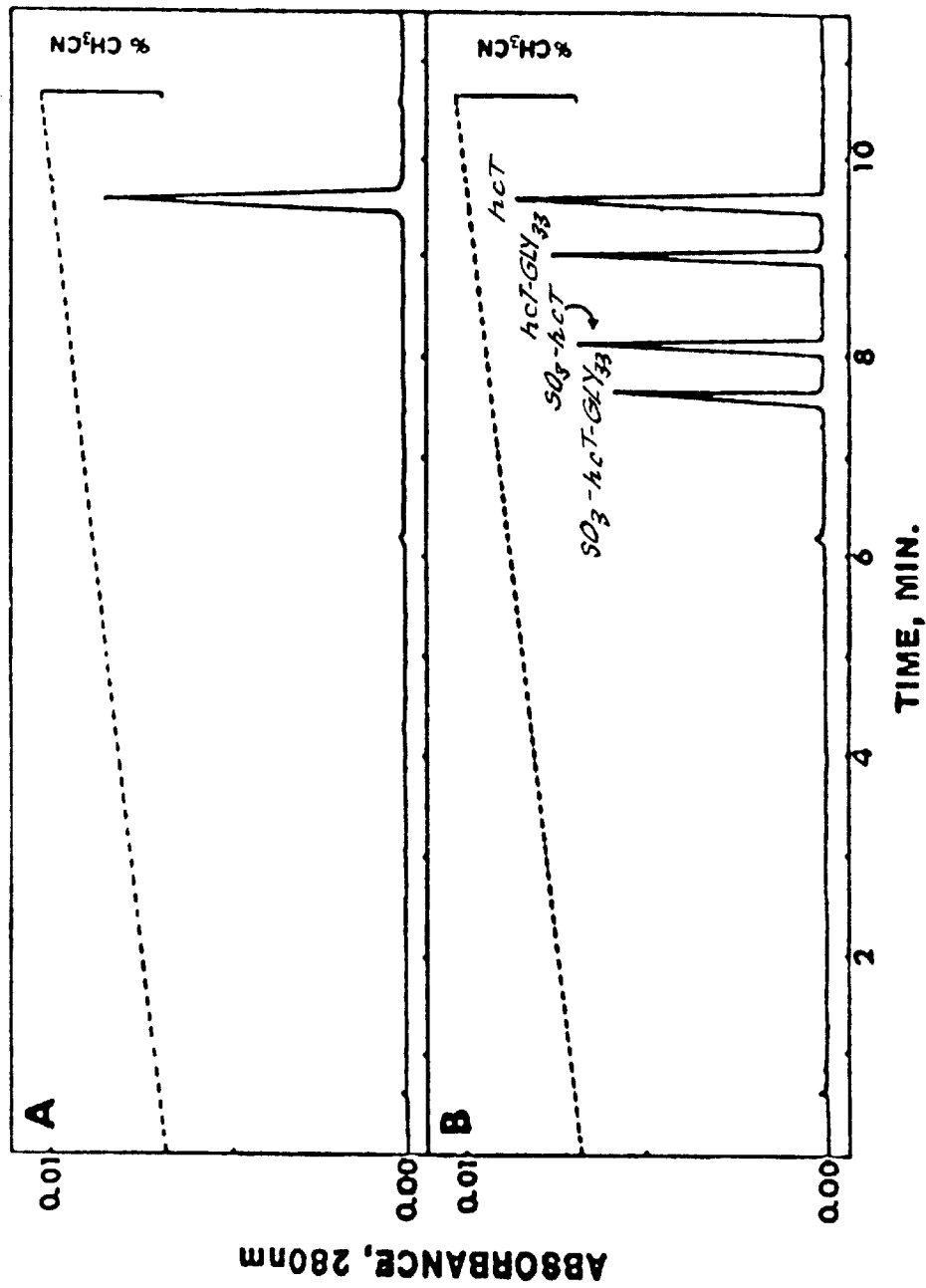

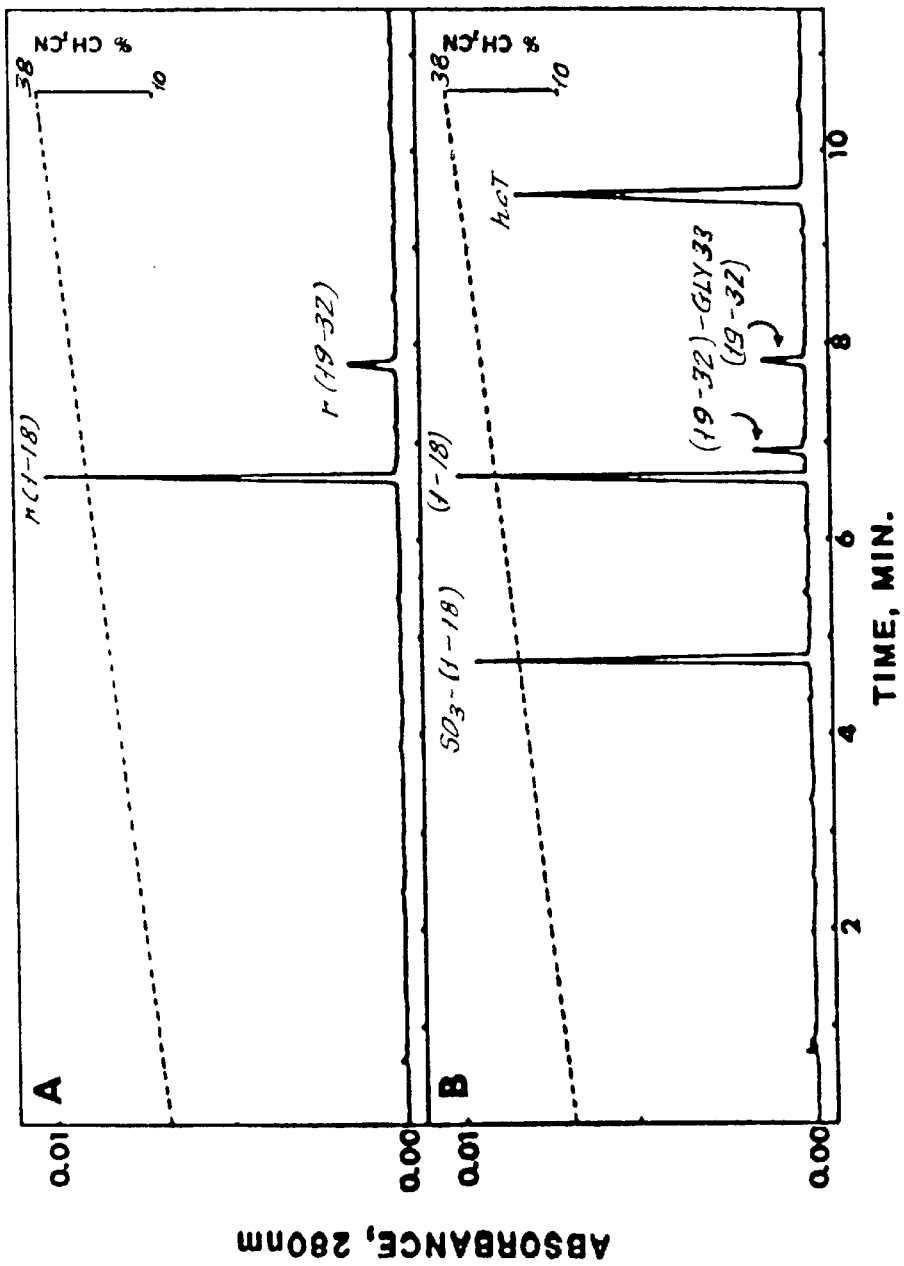

FIG. XII.

AMINO ACID COMPOSITION OF SYNTHETIC & RECOMBINANT HUMAN CALCITONIN (hCAT)

| Amino Acid | Recombinant hCT-Gly$_{33}$ | Recombinant hCT | Synthetic hCT | Residues From Sequence |
|---|---|---|---|---|
| ASX | 2.78 | 2.96 | 3.01 | 3 |
| GLX | 2.12 | 2.08 | 2.03 | 2 |
| SER | 1.03 | 0.80 | 0.78 | 1 |
| GLY | 4.97 | 4.11 | 4.18 | 4 |
| HIS | 0.97 | 0.99 | 1.06 | 1 |
| ARG | 0.00 | 0.00 | 0.00 | 0 |
| THR | 4.52 | 4.82 | 4.67 | 5 |
| ALA | 2.07 | 2.08 | 2.05 | 2 |
| PRO | 2.03 | 2.11 | 2.07 | 2 |
| TYR | 0.93 | 0.98 | 0.96 | 1 |
| VAL | 1.09 | 1.06 | 1.03 | 1 |
| MET | 1.00 | 0.99 | 0.98 | 1 |
| CYS | 1.58 | 1.82 | 1.78 | 2 |
| ILE | 1.01 | 1.02 | 1.01 | 1 |
| LEU | 2.15 | 2.13 | 2.10 | 2 |
| PHE | 2.92 | 3.00 | 3.07 | 3 |
| LYS | 1.03 | 0.99 | 1.00 | 1 |
| TRP | N.D. | N.D. | N.D. | 0 |
|  |  |  |  | 32 |

Samples (100-500 pMOL) were hydrolyzed with constant boiling HCl at 150°C for 1 hr. Tryptophan content was not determined (N.D.).

BIOASSAY

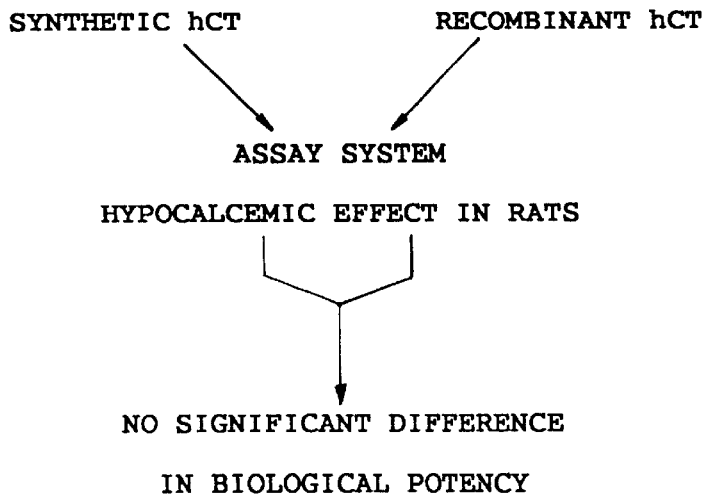

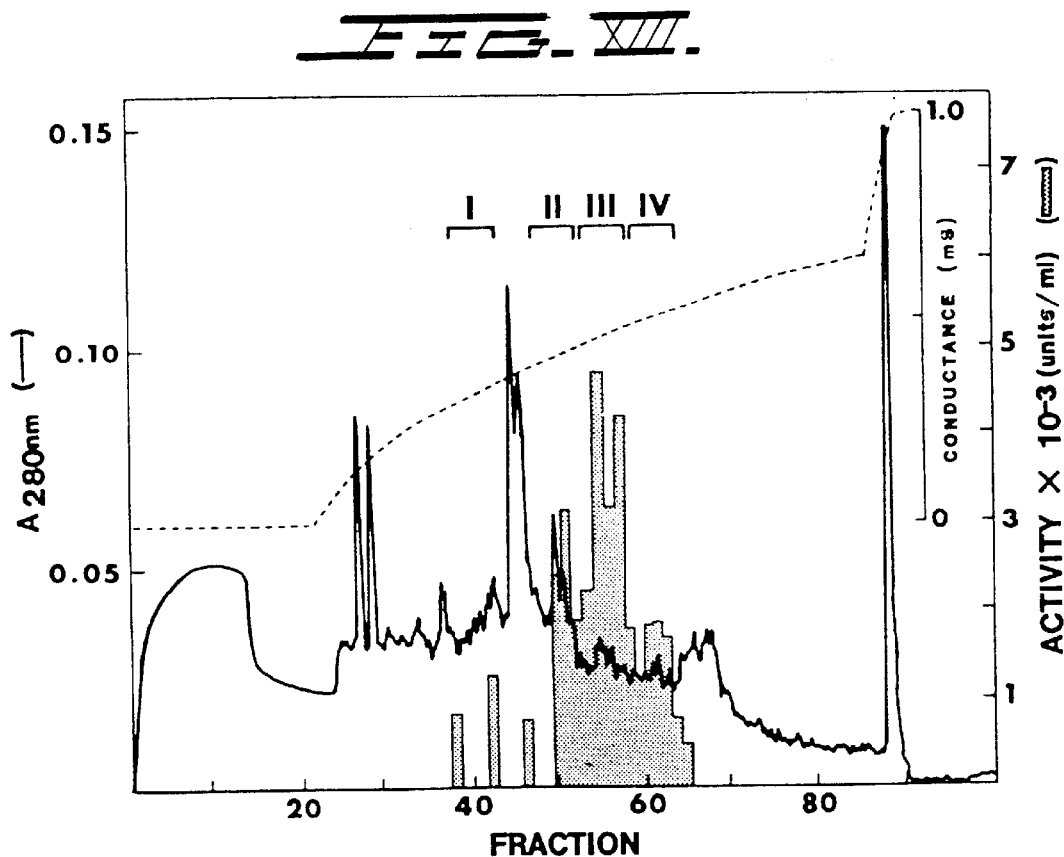
FIG. XIII.
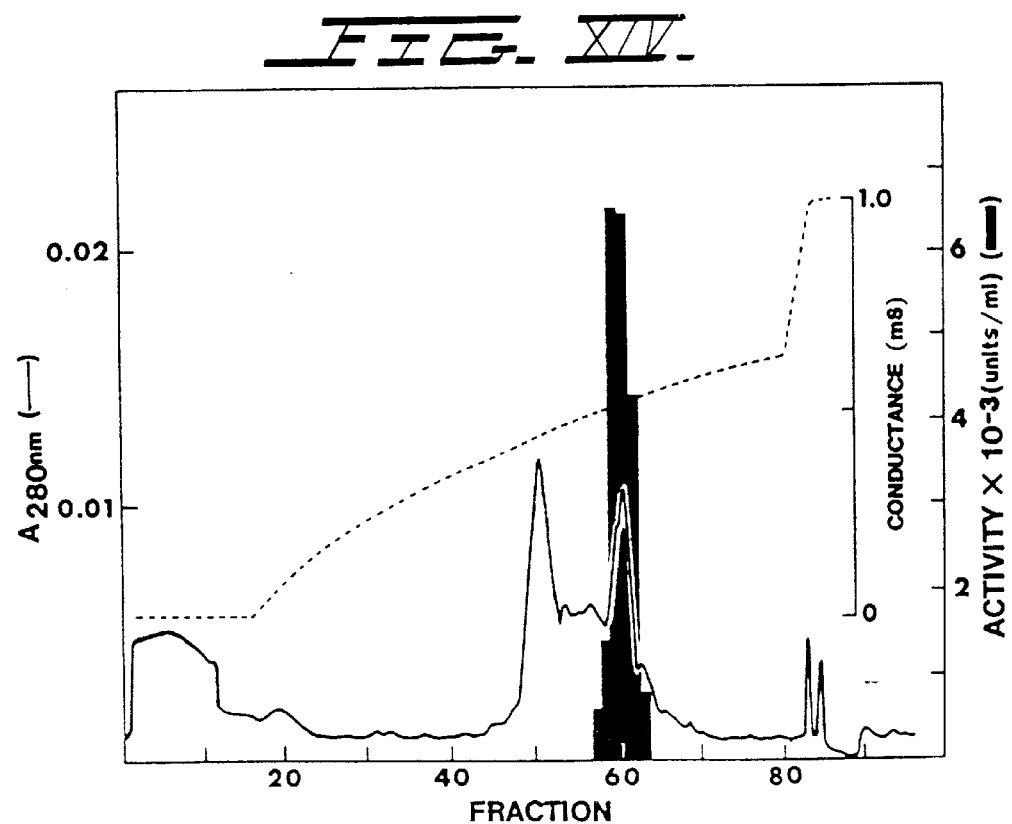
FIG. XIV.

FIG. XVa.
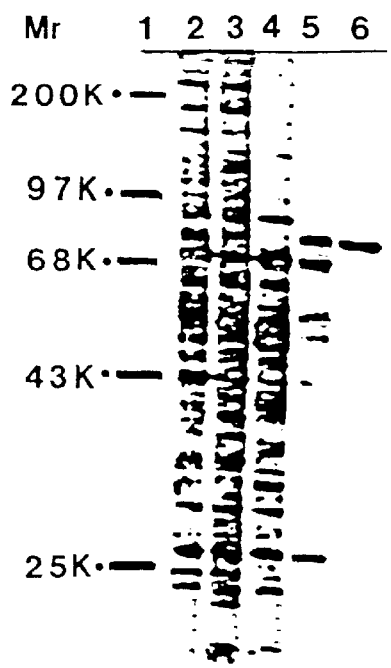
FIG. XVb.
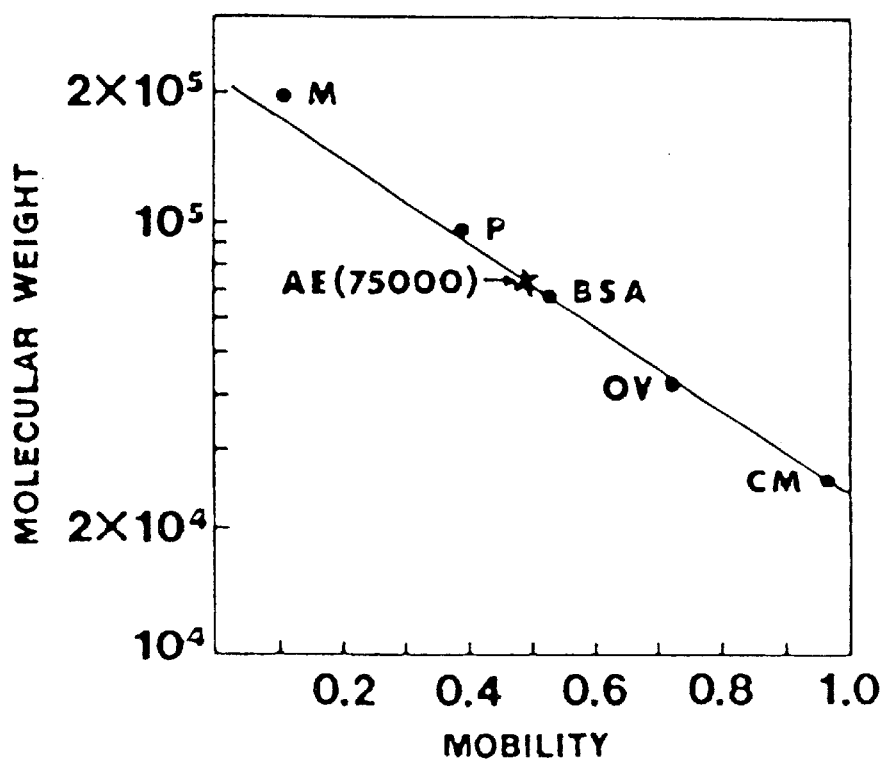

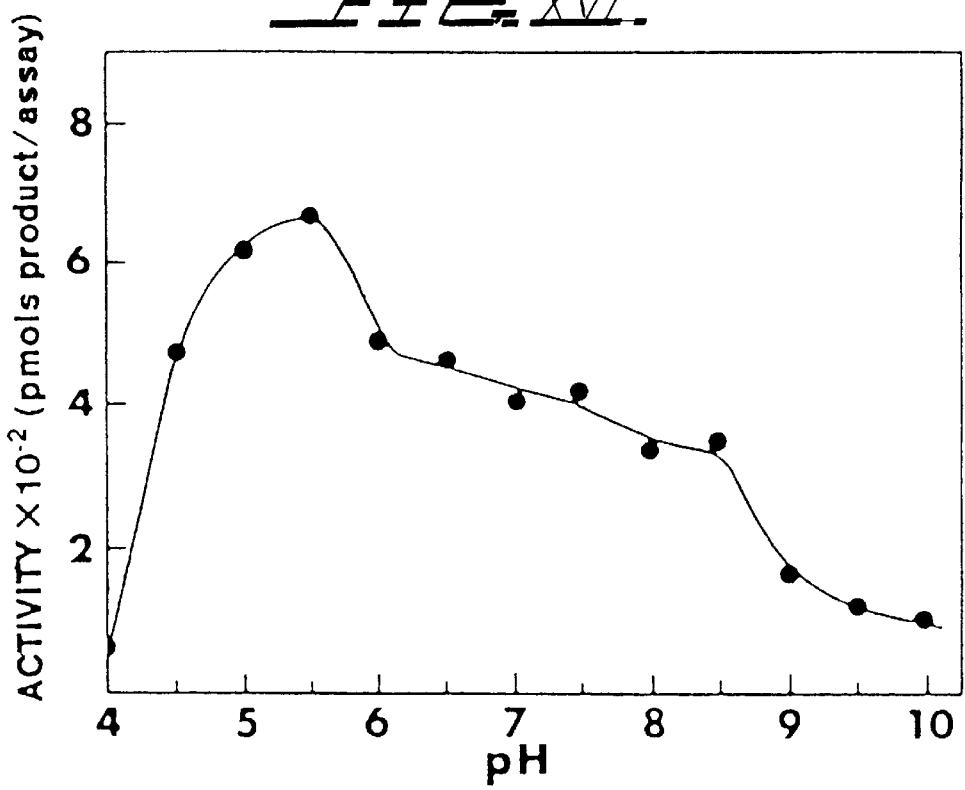
FIG. XVI.
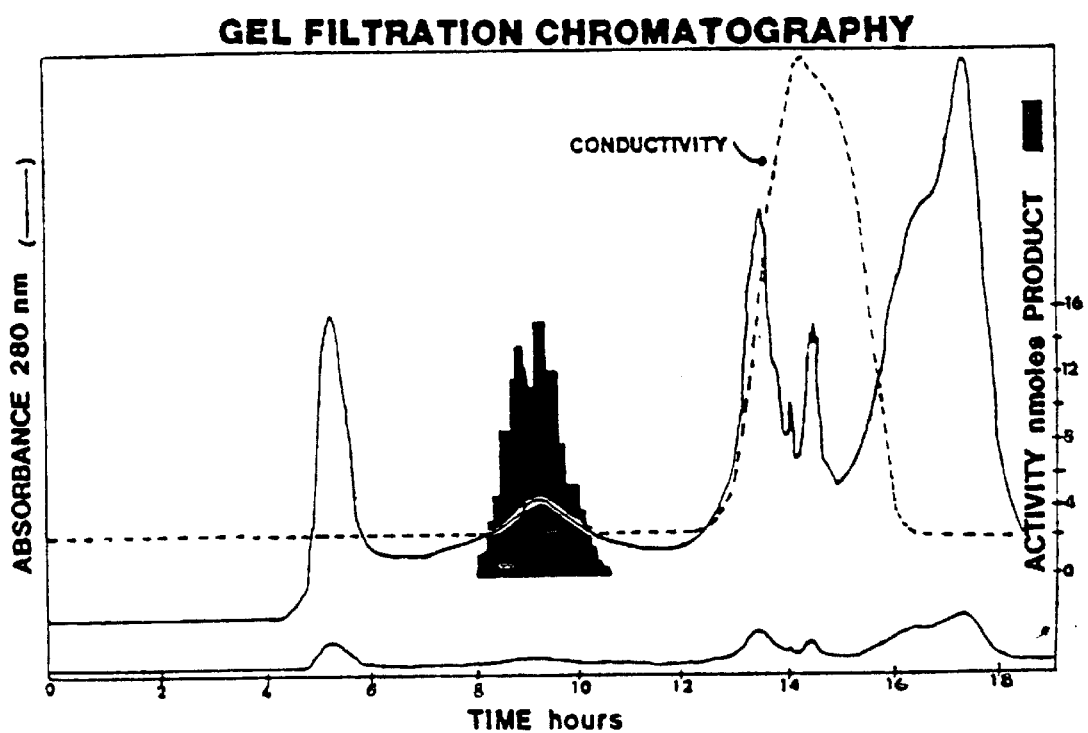
FIG. XVII.

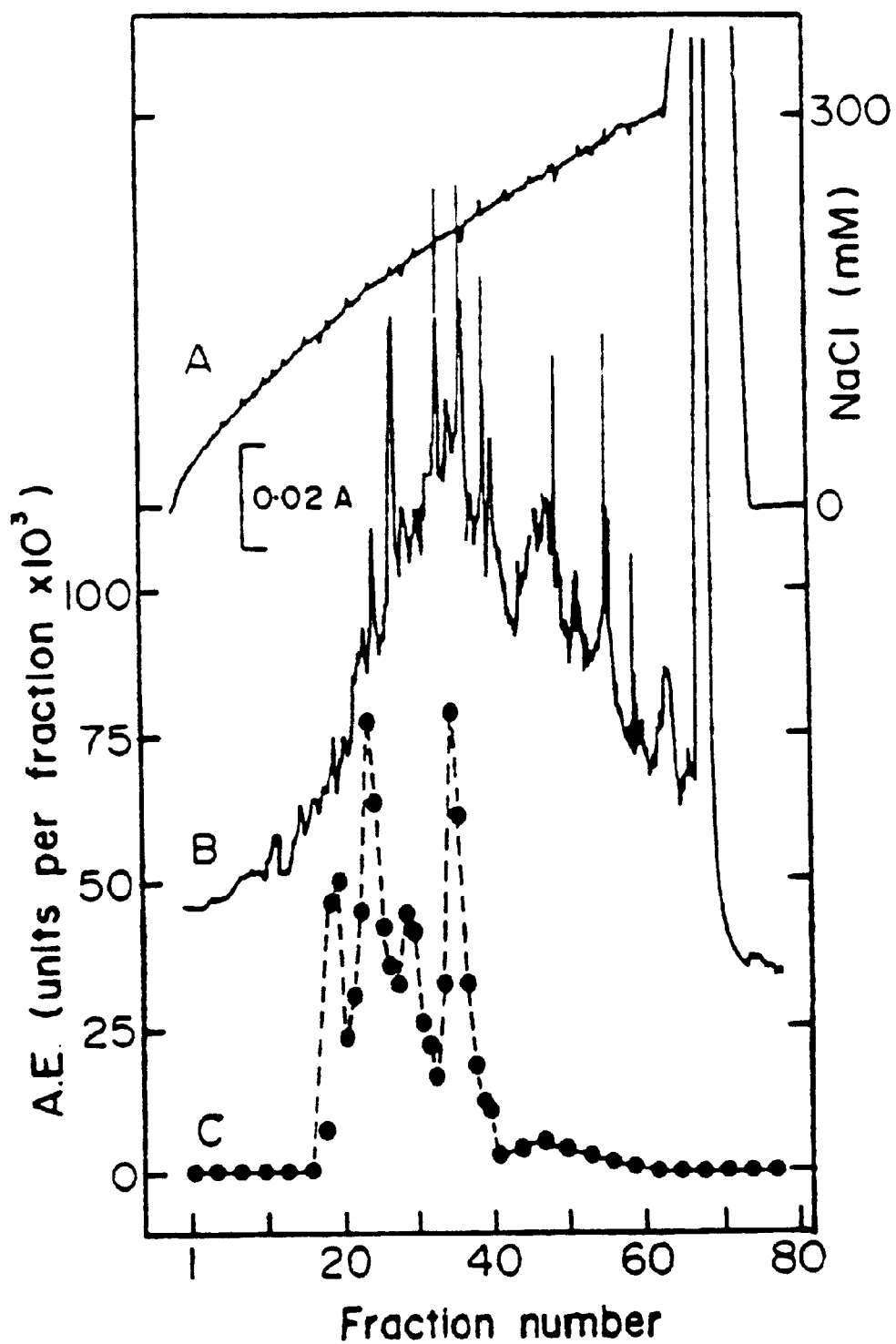
FIG. XVIII.

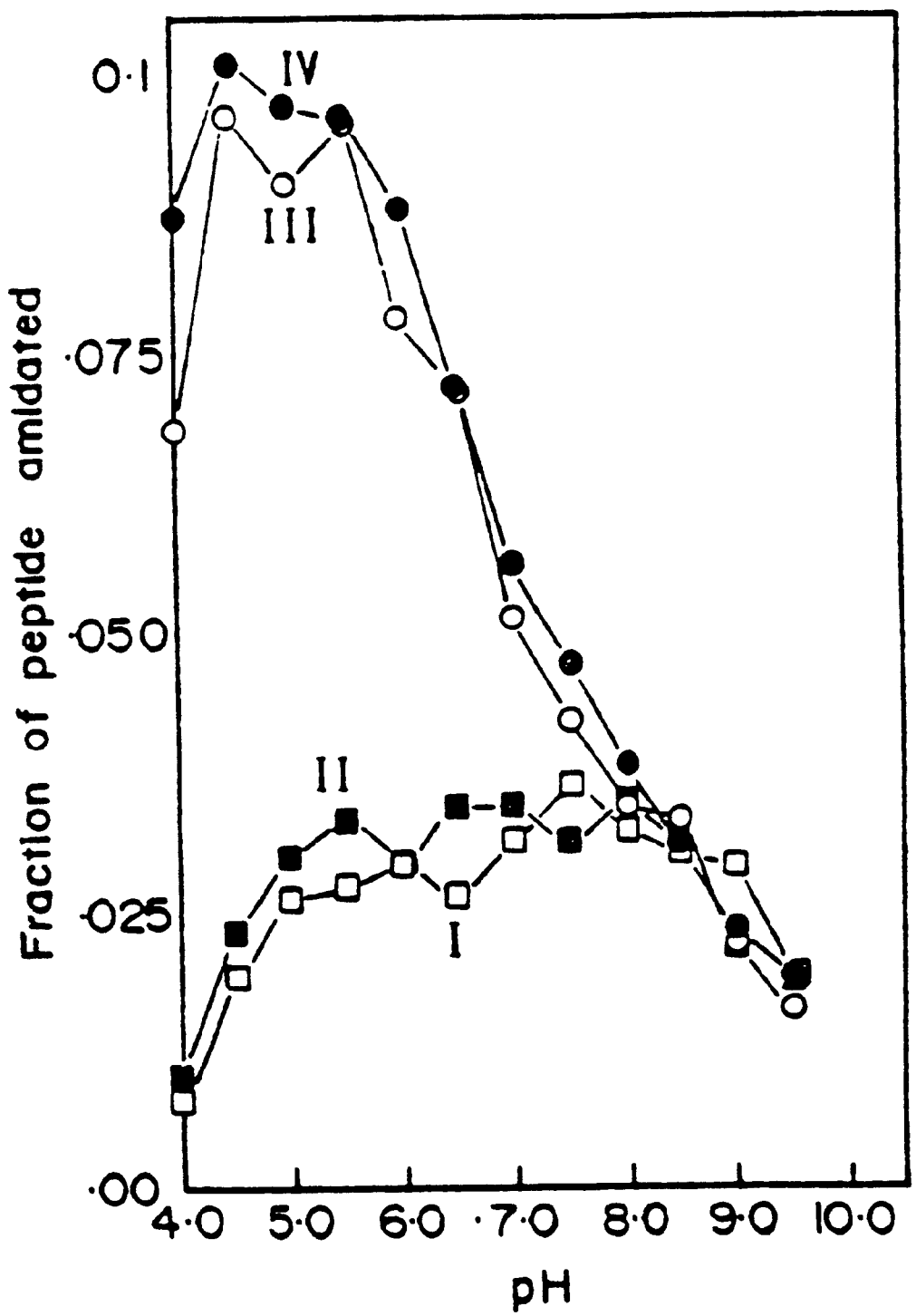
FIG. XIX.

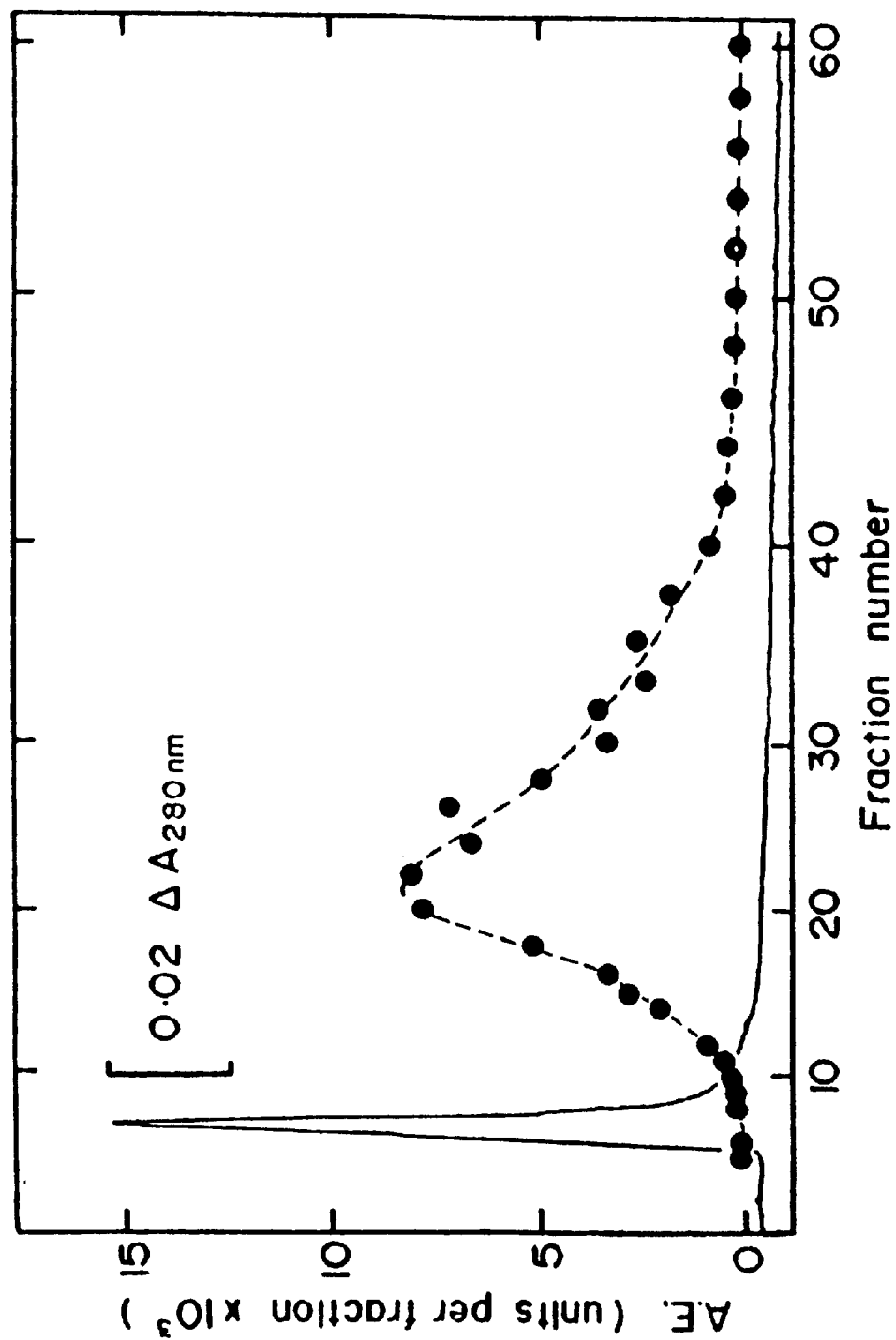
FIG. XX.

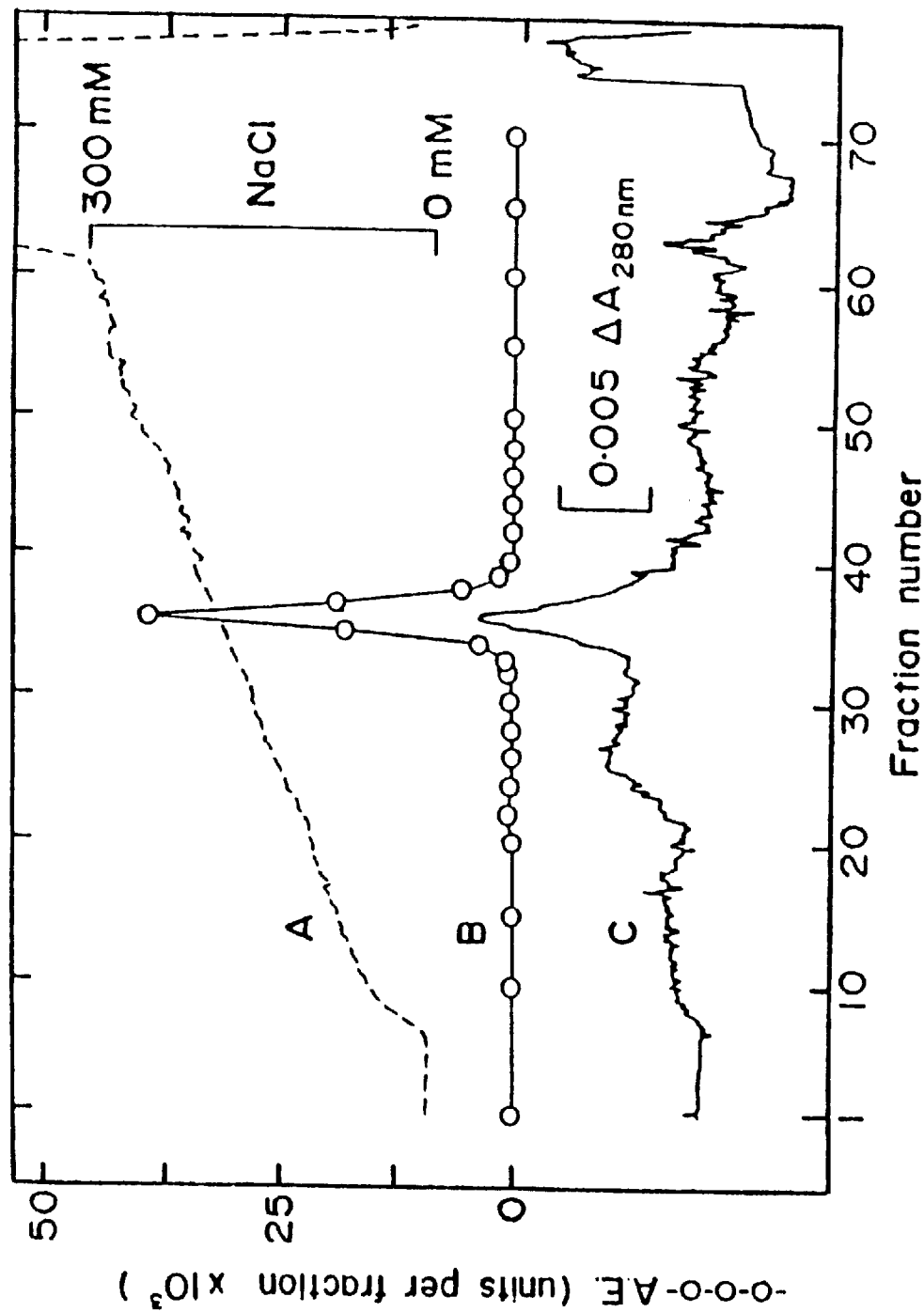
FIG. XXI.

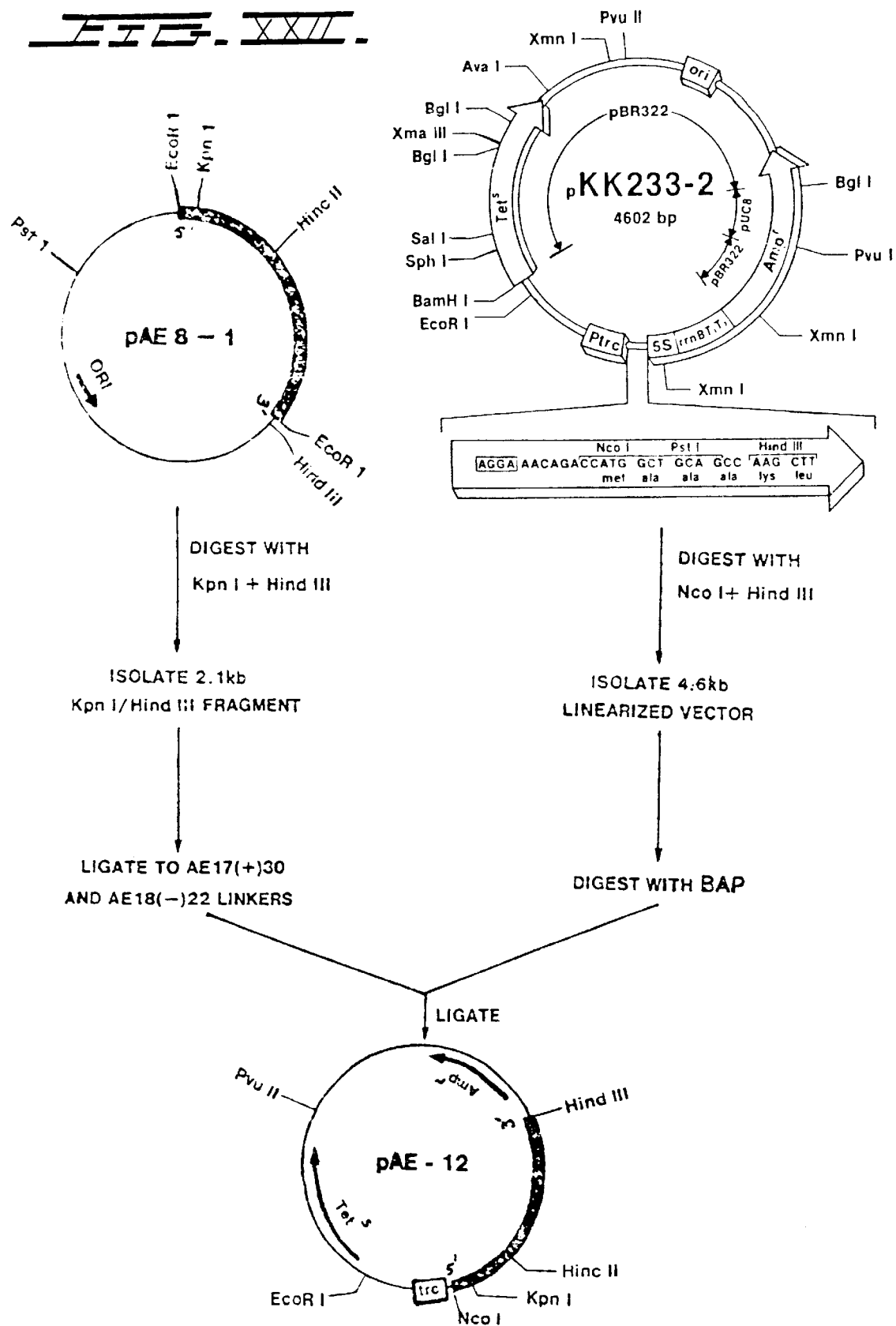

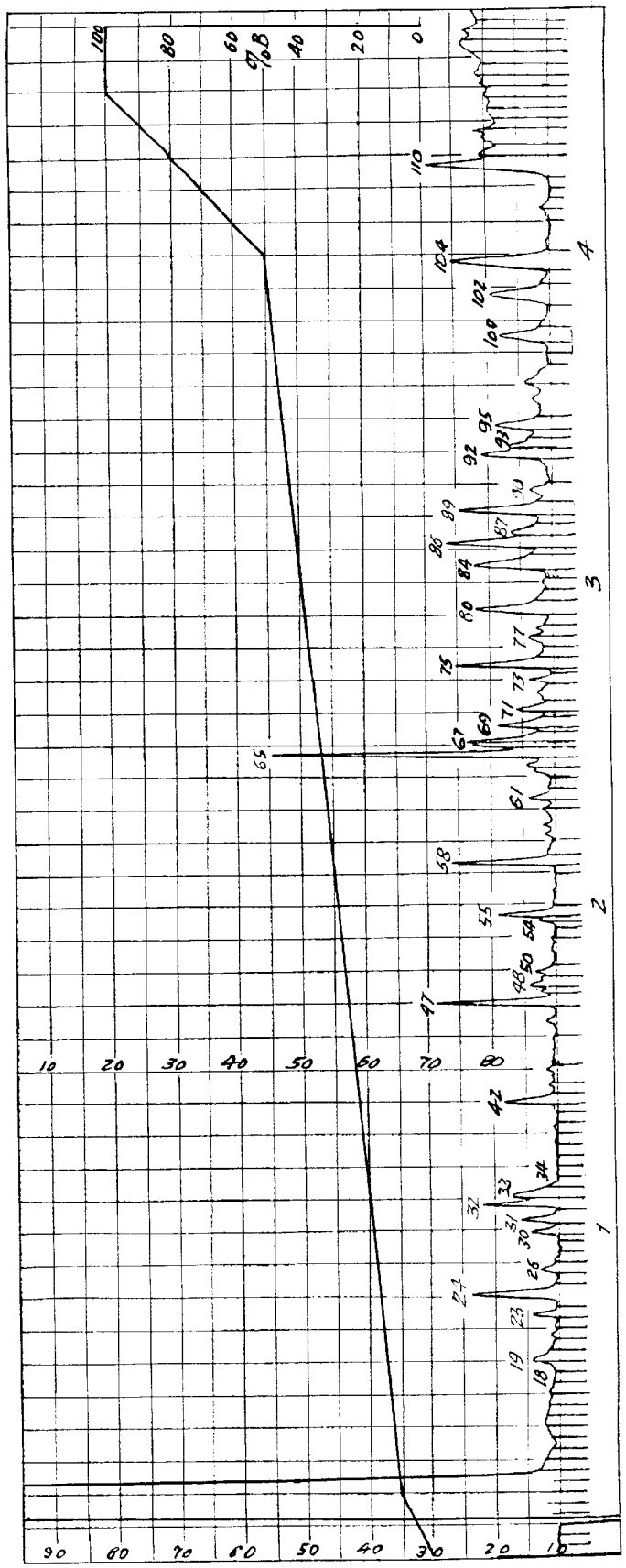

ALPHA-AMIDATING ENZYME COMPOSITIONS AND PROCESSES FOR THEIR PRODUCTION AND USE

RELATED APPLICATION

This application is a continuation-in-part of U.S. patent application Ser. No. 655,366, filed on Sep. 27, 1984, now U.S. Pat. No. 4,708,934, the entire disclosure of which is incorporated herein by reference.

BACKGROUND OF THE INVENTION

1. Field of the Invention

This invention relates to alpha-amidating enzymes, the production of alpha-amidating enzymes and their use in the production of alpha-amidated products by action of the enzymes on glycine-extended substrates. In certain preferred embodiments, the alpha-amidating enzyme of the invention may be used in the production of useful alpha-amidated hormones and products for agricultural or medical use including calcitonins, growth hormone releasing factors, calcitonin gene-related peptides, and other alpha-amidated products.

2. Prior Art

The intracellular processing (cleavage and/or functional group modification) of precursor forms of native proteins following their translation from nucleic acid coding sequences has been clearly documented.

In general, mammalian cells and other eukaryotes can perform certain post-translational processing procedures, while prokaryotes can not. Certain prokaryotes, such as E. coli, are widely employed as hosts for the production of mammalian proteins via recombinant DNA (rDNA) technology because they can be readily grown in batch fermentation procedures and because they are genetically well-characterized. However, many mammalian proteins produced by genetic engineering technology require some type of post-translational processing, and this must often be accomplished by using complex, in vitro chemical procedures which are cost-prohibitive for large-scale production applications.

One type of processing activity involves the specific amidation of the carboxyl-terminal amino acid of a protein. Many naturally-occurring hormones and peptides contain such a modification, which is often essential if the protein is to be biologically active. An example is calcitonin, where the substitution of a non-amidated proline residue for the amidated proline of the native form results in a 3,000-fold reduction in biological activity.

An agent which effects this C-terminal (alpha) amidation recognizes a glycine residue which immediately follows the amino acid to be amidated (R-X-gly, where R is the main body of the protein, X is the residue which is amidated, and "gly" is the glycine residue). The glycine is cleaved and actually donates the amino moiety to the penultimate amino acid, thereby amidating it.

The first authors to report an approximate molecular weight for an alpha-amidating enzyme were Bradbury A. F., et al., Nature, Vol. 298, 1982, p. 686–88. Using Sephadex G-100 they suggested a minimum apparent molecular mass of approximately 60,000 daltons.

Subsequent studies have suggested the molecular mass of such an enzyme to be between 60,000 and 70,000 daltons (as measured by gel filtration chromatography). These include Husain, I., and Tate S. S., FEBS Letters, Vol. 152 #2, 1983, p. 277–281; Eipper, et al., PNAS Vol. 80, 1983 p. 5144–5148; Gomez et al., FEBS Letters, Vol. 167, #1, 1984, p. 160–164, and Kizer, J. S., et al., PNAS, Vol. 81, 1984, p. 3228–3232.

Eipper et al., PNAS, Vol. 80, 1983, p. 5144–48, have reported that in addition to molecular oxygen, two co-factors are required for maximal enzyme amidation activity; these are ascorbic acid and copper (II) ion.

The chemical reaction resulting in the amidation of the carboxyl-terminus of a peptide requires a source for the amino group. Bradbury, A. F., et al., Nature, Vol. 298, 1982, p. 686–688, demonstrated that glycine is cleaved and donates the amino moiety to the penultimate amino acid, resulting in the amidation of the latter. The requirement for glycine as the amino group donor has been substantiated by other authors.

Landymore, A. E. N., et al., BBRC Vol. 117, #1, 1983, p. 289–293 demonstrated that D-alanine could also serve as an amino donor in the amidation reaction. Subsequent work by Kizer et al., PNAS, Vol. 81, 1984, p. 3228–3232, showed two distinct enzyme activities in rat brain which were capable of catalyzing the alpha-amidating reaction. The higher molecular mass species (70,000 daltons) has a specificity restricted for glycine at the carboxyl-terminus of the substrate. The lower molecular mass enzyme accepts a substrate with $\beta$-alanine as the carboxyl-terminal amino acid.

The pH optimum for the alpha-amidating enzyme extracted and partially purified from porcine pituitary was reported by Bradbury A. F., and Smythe D. G., BBRC, Vol. 112, #2, 1983, p. 372–377 to be approximately 7.0. Eipper, B. A., et al., PNAS, Vol. 80, 1983, p. 5144–5148, corroborated these results by reporting a pH optimum of 7 for an alpha-amidating enzyme which was partially purified from rat pituitaries. They also noted that enzyme activity declined rapidly at pH levels below 6.5 or above 7.5.

In all of the aforementioned publications, (incorporated herein by reference), the extracts and partially purified enzyme mixtures described contain additional proteolytic enzymes capable of degrading potential substrates and products as well as alpha-amidating enzymes themselves, thus retarding the amidation by such enzymes of peptides and polypeptides purified from natural sources or produced by recombinant DNA techniques.

Broadly, all amidation activities previously measured by others were based upon the conversion of D-substrates such as a tripeptide, D-Tyr-Val-Gly-COOH to D-Tyr-Val-$CONH_2$. Of the two possible configurations ("D" or "L"), naturally-occurring, biologically important amino acids occur in the "L" form. However, use of the "D" form by these other investigators was necessitated to counteract the presence of extraneous proteolytic enzymes in the impure amidating enzyme preparations used by these researchers. These extraneous enzymes may have a pronounced proteolytic effect on L-amino acid substrate while having little effect on a D-substrate. The investigators, saddled with proteolytic and other impurities in their enzyme, used unnatural "D" substrate in order to avoid some of the effects of the impurities. No one prior hereto has been able to demonstrate that their enzyme preparations can efficiently amidate any physiologically relevant substrates, i.e., L-substrates for conversion to biologically active alpha-amidated L-products.

As demonstrated herein, the preparations of this invention are capable of effectively amidating L-substrates and, on D-substrates, have an activity of from 60 to more than 1,000 times greater than the highest activity noted in any Prior Art of which applicants are aware.

Enzymatic preparations capable of amidating the carboxyl-terminus of peptides and proteins have been described from a variety of sources. For instance, Bradbury, A. F., et al., Nature Vol. 298, 1982, p. 686–688 (the entire disclosure of which is incorporated herein by reference) reports an alpha-amidating enzyme activity to be present in porcine pituitary. The preparation of porcine pituitary containing the enzyme has the ability to convert peptides that terminate in a glycine to the corresponding desglycine peptide amide. Bradbury et al. acknowledges, however, that the preparations will not amidate peptides or polypeptides purified from natural sources:

> "An assay system for detecting and estimating amidating activity in pituitary was obtained by examining the ability of enzyme preparations to convert the synthetic tripeptide D-tyrosylvalylglycine to the corresponding dipeptide amide D-tyrosylvaline amide . . . The D-tyrosine residue conferred stability against degradation by aminopeptidases present in tissue homogenates . . . Control experiments showed that when synthetic . . . D-tyrosylvaline amide was incubated in the same conditions it was slowly degraded. Thus the formation of the dipeptide amide by the pituitary enzyme is followed by its destruction by other enzymes present in the pituitary extract." (page 686)

Thus, Bradbury et al. acknowledges that the preparations described contain other proteolytic enzymes which degrade the peptide or polypeptide and that the non-naturally occurring D-tyrosine residue was utilized to minimize such degradation.

Further, Bradbury et al. teaches the use of homogenization or sub-cellular fractionation followed by gel filtration chromatography to purify an amidating enzyme that, admittedly, remains contaminated with proteolytic enzymes.

Husain, I., and Tate, S. S., FEBS Letters, Vol. 152, #2, 1983, p. 277–281, describe an alpha-amidating activity present in bovine pituitary neurosecretory granules.

Eipper et al., PNAS Vol. 80, 1983, p. 5144–5148, reported an alpha-amidating enzyme activity to be present in the anterior, intermediate and posterior lobes of the rat pituitary gland and bovine intermediate pituitary. However, this reference only teaches the utilization of synthetic D-Tyr-Val-Gly substrate to search for alpha-amidation activity, a recognition of the impurity of the preparations produced.

Gomez et al., FEBS Letters, Vol. 167, #1, 1984, p. 160–164 determined that rat hypothalamus also contained an alpha-amidating enzyme activity.

Bradbury, A. F., Smythe, D. G., in Peptides Structure and Function: Proceedings of the Eighth American Peptide Symposium; p. 249–52 (1983), Editors Hruby, V. J., and Rich, D. H., describe the presence of an alpha-amidating enzyme activity in rat thyroid glands.

Mains R. E. et al., Endocrinology, Vol. 114, 1984, p. 1522–1530, reported that a murine cell line derived from the anterior pituitary lobe (ATT-20) contained an alpha-amidating enzyme activity that apparently decreased with time in culture.

Glands or organs known to contain amidated peptides may contain an enzyme capable of catalyzing the amidation reaction. For example, lower life forms such as the dog fish (*Squalus acanthias*) have been reported by O'Donohue T. L., et al., Peptides 3, 1982, p. 353–395, to contain amidated peptides in pituitary extracts. Scheller, R. H. et al., Cell, Vol. 32, 1983, p. 7–22 reported the presence of amidation signal peptides in the marine snail Aplysia. Despite the apparent ubiquitous distribution of this activity in nature, little information has been published on the physicochemical characteristics of the enzyme. This may be attributed to the very low levels of enzyme present in these neuroendocrine organs.

The presence of amidated peptides in a particular tissue is not necessarily synonymous with high levels of alpha-amidating enzyme. For example, rat anterior pituitary tissue contains high alpha-amidating activity but no known substrates [Eipper et al., PNAS 80, 5144–5148 (1983)]. Rat posterior pituitary tissue contains amidated peptides (oxytocin and vasopressin) but has very little alpha-amidating activity [Eipper et al., Endo 116, 2497–2504 (1985)]. Therefore, until individual tissues are tested for alpha-amidating activity, the presence or potential levels of the enzyme can not be anticipated.

OBJECTS AND SUMMARY OF THE INVENTION

It is an object of this invention to provide alpha-amidating enzymatic compositions which can efficiently produce useful alpha-amidated products even from substrates containing L-amino acids such as peptide or polypeptide substrates purified from natural sources or produced by recombinant DNA techniques.

It is a further object to provide effective and cost-efficient methods for production of the enzymatic composition.

It is a further object to provide monoclonal antibodies specific for alpha-amidating enzyme, and immobilized antibodies, purification resins, immunoaffinity columns and the like which, utilizing said antibodies, efficiently purify alpha-amidating enzyme.

It is a further object to provide genetically engineered host cells capable of high-yield expression of alpha-amidating enzyme.

It is a further object of this invention to prepare alpha-amidated products from substrates containing a C-terminal glycine residue by reacting the substrate in the presence of the enzyme composition.

These and other objects will become apparent from a thorough reading of the present disclosure. In accordance with the invention, applicants provide novel alpha-amidating enzyme compositions of sufficient purity to exhibit a specific alpha-amidating activity of at least about 25 mU per mg of protein present in said enzymatic composition, and preferably above 50 or above 150 mU/mg protein. All specific activity units set forth herein are based upon the conversion of Dansyl-D-Try-Val-Gly-COOH to Dansyl-D-Tyr-Val-CONH$_2$. One mU is defined as the amount of activity needed to convert one nanomole (nmole) of Dansyl-D-Tyr-Val-Gly-COOH to one nmole of Dansyl-D-Tyr-Val-CONH$_2$ per minute at 37° C. and pH 7.0 in the presence of ascorbate ions at a concentration of 3 mM (based on total reaction mixture including enzyme, substrate, co-factors, etc.), molecular oxygen in a molar excess over substrate and a concentration of cupric ions effective to maximize activity (usually about 2 $\mu$M depending on the state of purity of the enzyme).

Alpha-amidating enzymes of the invention, such as peptidyl glycine alpha-amidating monooxygenase, are capable of catalyzing the conversion of a peptidyl compound having a glycine residue at least at the C-terminus of a peptide chain to a corresponding peptidyl amide compound having an amino group in place of the C-terminal glycine. As used herein, the term "peptide chain" means any polypeptide having at least two amino acids joined together by a peptide bond. The term "peptidyl compound" includes any compound having a peptide chain. The term "corresponding peptidyl amide" refers to any product of a reaction which substitutes an amino group in place of a C-terminal glycine of a peptide chain.

It is preferred that the alpha-amidation reaction take place in the presence of oxygen and a reducing agent. Useful reducing agents include but are not limited to ascorbic acid, ascorbic acid salts, dihydroxyfumarate, metallic cyanide compounds, and tetrahydropterin. Certain co-factors have been found to aid the progress of the reaction and/or to retard degradation or inactivation of the enzyme. These co-factors include, but are not limited to, catalase, ethanol, potassium iodide, and cupric ions. The purified enzymatic compositions of the invention are preferably sufficiently free of proteolytic activity capable of degrading either the alpha-amidating enzyme or the products or reactants of the alpha-amidation reaction, so that the enzymatic compositions can catalyze the alpha-amidation reaction even when the substrate and product are comprised of L-amino acids. Proteolytic activity in the amidation reaction mixture may not directly reflect the concentration of protease. Activity, even at high protease concentrations, may be suppressed, for instance, by action of various inhibitors. The lack of proteolytic activity which increases the enzymatic composition's commercial and practical desirability for use with substrates comprised of L-amino acids does not in any way diminish the composition's attractiveness for use with substrates which do not contain L-amino acids.

As set forth further in the detailed description, applicants have purified numerous specific protein species which possess substantial alpha-amidating activity. "Alpha-amidating activity" as used herein means any activity tending to leave only an amino group in a position previously occupied by a C-terminal glycine of a substrate peptidyl compound. Such a substitution may involve cleavage of all but the amino group of glycine such that only an amino group remains in the position previously occupied by the entire glycine moiety. "Alpha-amidating enzyme", as used herein, refers to any composition or compound which exhibits alpha-amidating activity, and to active homologs and fragments thereof.

Enzymatic compositions purified in accordance with the instant invention may be purified until homogeneous. As used herein, "homogeneous" refers to enzyme preparations exhibiting a single, well-defined band following electrophoresis on a sodium dodecyl sulfate/polyacrylamide gel and exhibiting single amino acid sequence data in response to common sequencing methods.

Certain alpha-amidating enzymes purified to homogeneity in accordance with the instant invention have exhibited specific enzyme activities above about 1500 mU/mg protein.

Enzymatic compositions prepared in accordance with the instant invention may be used in the production of useful alpha-amidated peptidyl products by using the enzymatic compositions to catalyze the alpha-amidation of such products. A substrate is provided which is a peptidyl compound having a glycine residue at least at the C-terminus of a peptide chain wherein substitution of an amino group for the C-terminal glycine results in the desired product. The substrate is reacted, preferably in the presence of oxygen and a reducing agent, in the presence of an enzymatic composition prepared in accordance with the instant invention for a time period sufficient to convert the peptidyl compound to a corresponding peptidyl amide. Conversion begins substantially at first contact of substrate and enzyme but reaction velocity varies considerably with pH, temperature, identity of substrate, concentration of co-factors, and other parameters which may be adjusted in a known manner to optimize the reaction. The reaction is usually allowed to progress for a time chosen in view of the desired conversion percentage (of substrate to product). In preferred embodiments, co-factors such as those previously discussed, are used to aid the progress of the reaction and/or enhance or sustain the activity of the enzyme.

Numerous useful products including natural hormones and the like, for which alpha-amidation is preferred or necessary, may be made by reacting glycine-extended peptidyl compounds in the presence of alpha-amidating enzyme compositions in accordance with the present invention. These products which may be used, for instance, in agriculture or in the treatment of diseases characterized by hormonal deficiencies, include but are not limited to various calcitonins, growth hormone releasing factors, calcitonin gene-related peptides, and the like. Hormones referred to herein such as the foregoing calcitonins, growth hormone releasing factors and calcitonin gene-related peptides, include C-terminal amide protein species which display the characteristic activity of the named hormone as understood by those skilled in the art. For instance, calcitonin includes all species which display the regulation of calcium uptake into bone which is characteristic of known calcitonins. Homologs of the various protein species discussed herein are included with the definitions of the species, and any nucleotide sequences or amino acid sequences set forth herein are intended to include homologous sequences wherein substitutions, additions or deletions do not materially affect the function imparted by the sequence set forth. Preferably, at least about 40%, and most preferably 50% of the amino acids in a peptide correspond to those set forth. With respect to nucleotide sequences, codons may of course be substituted by equivalent codons coding for the same amino acids.

The ability of the enzyme compositions of the invention to catalyze the alpha-amidation reaction even on substrates comprising L-amino acids, enables the effective and cost efficient production of these products using substrates purified from natural sources or produced by recombinant DNA techniques.

In certain preferred embodiments, the alpha-amidation reaction may be facilitated by immobilizing the enzyme on a solid support which is insoluble in aqueous media and resistant to degradation under reaction conditions, and the passing substrate over the immobilized enzyme, preferably in the presence of appropriate co-factors. As used herein, "immobilizing" refers to bonding enzyme to support. Supports which may be useful for this purpose include but are not limited to control-pore glass, or an activated absorbant such as cyanogen bromide-activated sepharose. Enzymes immobilized in this manner may be reused by removing reaction mixture off the solid support which continues to retain enzyme for future use.

Applicants have discovered that enzymatic compositions in accordance with the invention may be obtained and purified by a number of methods. It has been found that medullary thyroid carcinoma tissue, preferably derived from a rat, cell lines thereof, and/or cell culture media from said cell lines are particularly desirable sources of crude alpha-amidating enzyme. Impure alpha-amidating enzyme may be purified by subjecting the crude composition to both size exclusion chromatography and anion exchange chromatography, preferably strong anion exchange chromatography. As used herein, "strong" anion exchange chromatography relates to anion exchange chromatography conducted on any resin that maintains a constant net positive charge in the range of pH 2–12. In certain preferred embodiments of the invention, size exclusion chromatography precedes the strong anion exchange chromatography, and the size exclusion chromatography step may even be preceded by yet another anion exchange chromatography step. A second strong anion exchange chromatography step subsequent to the first step may be desirable, and in one preferred embodiment, either the first strong anion exchange chromatography or the second strong anion exchange chromatography is conducted at a basic pH while the other is conducted at an acidic pH.

Using enzyme species which have been substantially purified to homogeneity in accordance with the instant invention, monoclonal and polyclonal antibodies specific for the enzyme have been prepared by using purified enzyme as an antigen to elicit immune response in mice and chickens respectively. Antibodies derived in this manner from any species may be purified and immobilized on a solid support for the purpose of producing an immunoaffinity column specific for the enzyme. This column may be used for purification of crude enzymatic material resulting in increased efficiency and reusability of enzyme.

Enzyme purified in accordance with the instant invention together with tryptic fragments thereof have been sequenced by known methods and sequence data has been used for the preparation of oligonucleotide probes. Using labeled oligonucleotide probes produced in this manner, applicants have isolated a gene coding for an alpha-amidating enzyme from a cDNA library synthesized from polyA RNA derived from rat medullary thyroid carcinoma tissue. The gene, which is more particularly characterized in the detailed description portion of this application, may be ligated into an appropriate expression vector, and transformed into any host cell capable of expressing the gene. Appropriate hosts include but are not limited to *E. coli*, yeast strains such as *S. cerevisiae*, or higher eukaryotic cells such as the cell line from which the enzyme was originally purified. Commercial mass production can be expected to be facilitated by a microorganism genetically engineered as set forth above to express large quantities of alpha-amidating enzyme.

Commercial mass production of the enzymes from natural sources may be facilitated by purification methods comprising both size exclusion chromatography and anion exchange chromatography wherein enzymatic species retained by the anion exchange chromatography column are eluted using a saline solution having a concentration above about 250 mM and preferably as high as 350 mM or 500 mM. At high saline concentrations, most retained enzyme species will be eluted. Size exclusion chromatography should be designed to isolate species with an apparent molecular weight between about 58,000 and 67,000 daltons and preferably between about 60,000 and 65,000 daltons. The purified preparation is capable of amidating a peptidyl compound which has been purified from natural sources or produced by recombinant DNA techniques, i.e. peptides comprised of L-amino acids.

BRIEF DESCRIPTION OF THE FIGURES

FIG. I is an elution profile of amidating enzyme from a Sephacryl S-300 column as measured by absorbance and enzyme activity.

FIG. II is an elution profile of amidating enzyme from a Mono Q HR 5/5 column at pH 6.0, as measured by absorbance and enzyme activity.

Figure 1:
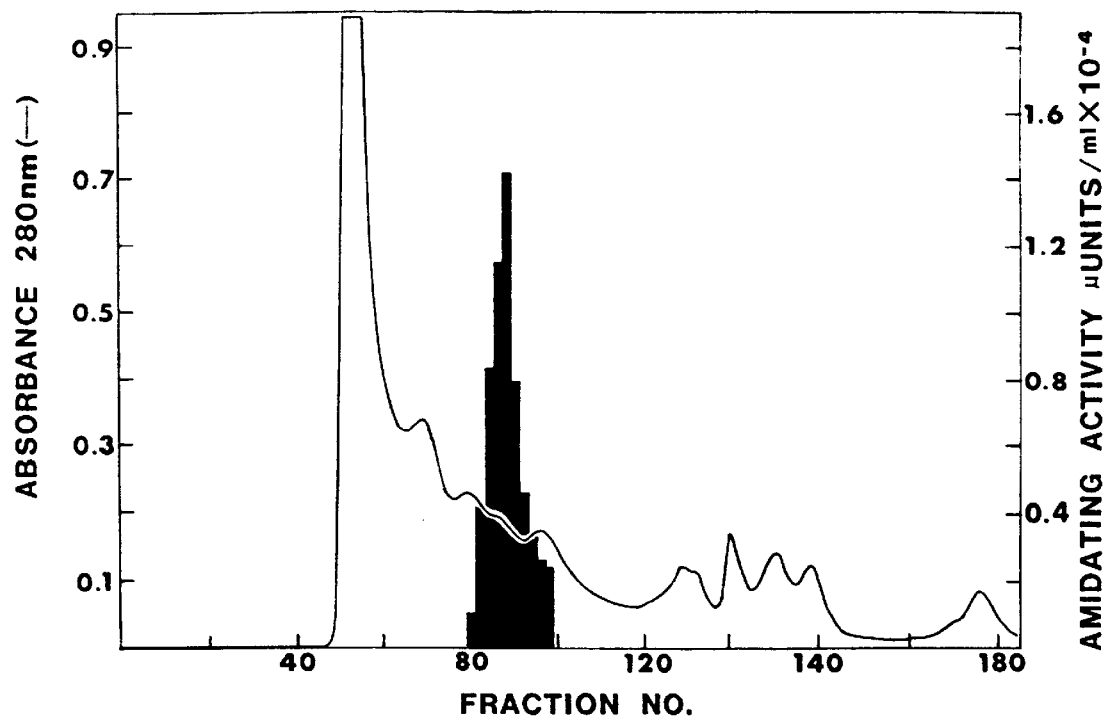

FIG. III is an elution profile of amidating enzyme from a first Mono Q column at pH 6.0 by a second Mono Q HR 5/5 column run at pH 8.0, as measured by absorbance and enzyme activity.

FIG. IV is an analysis of purified alpha-amidating enzyme by electrophoresis on a 10% denaturing polyacrylamide gel.

FIG. V is a verification of the identity of the purified alpha-amidating enzyme by electrophoresis on a non-denaturing 10% polyacrylamide gel, followed by determination of enzymatic activity by incubation of individual gel slices with substrate.

FIG. VI is a schematic of the steps employed in the production of recombinant human calcitonin by expression as a fusion protein followed by purification and amidation.

FIG. VII is a design of the fusion protein gene for the recombinant expression of glycine-extended human calcitonin in microorganisms.

FIG. VIII is an elution profile of sulfonated glycine-extended human calcitonin from a reverse-phase HPLC column as measured by absorbance and a calcitonin-specific immunoassay, demonstrating separation of hCT from its fusion partner.

FIG. IX is an elution profile of recombinant human calcitonin from a reverse phase HPLC column as measured by relative fluorescence, following amidation and removal of S-sulphonate.

FIGS. X(A–B) is a characterization of purified amidated recombinant human calcitonin by retention time on reverse phase HPLC (Panel A) compared to human sCT fragment standards (Panel B).

FIGS. XI(A–B) is a characterization of purified amidated recombinant human calcitonin by analysis of fragments following tryptic digestion (Panel A) compared to human sCT fragment standards (Panel B).

FIG. XII is a comparison of amino acid content, and of biological activity, of purified amidated recombinant human calcitonin versus synthetic human calcitonin.

FIG. XIII is an elution profile showing separation of multiple forms of alpha-amidating enzyme (Peaks I, II, III, and IV) by chromatography on a Mono Q HR 10/10 column at pH 6.0 using an expanded linear salt gradient.

FIG. XIV is an elution profiled of Peak III alpha-amidating enzyme by strong anion exchange chromatography on a Mono Q HR 10/10 column at pH 8.0, as measured by absorbance and enzyme activity.

FIGS. XV(A–B), Panel a is a characterization of purified Peak III alpha-amidating enzyme by 7% denaturing polyacrylamide gel electrophoresis (lane 6). Panel b is a calculation of molecular weight of Peak III alpha-amidating enzyme by comparison to the mobility of marker proteins on a 7% denaturing polyacrylamide gel.

FIG. XVI is a graph of enzyme activity versus pH for determination of the pH optimum for Peak III alpha-amidating enzyme using dansyl Tyr-Val-Gly as the substrate.

FIG. XVII is an elution profile of alpha-amidating enzyme from CA-77 Cell Tissue Culture Medium on a Sephacryl 300-SF column, as measured by absorbance and enzyme activity.

FIG. XVIII is an elution profile showing separation of multiple forms of alpha-amidating enzyme from CA-77 Cell Tissue Culture Medium by strong anion-exchange chromatography on a Mono Q HR 10/10 column at pH 6.0, as measured by absorbance and enzyme activity.

FIG. XIX is a graph of enzyme activity versus pH for determination of the pH optimum for each of the multiple forms of alpha-amidating enzyme from CA-77 Cell Tissue Culture Medium.

FIG. XX is an elution profile of Peak IV alpha-amidating enzyme from CA-77 Cell Tissue Culture Medium by Phenyl-Sepharose chromatography, as measured by absorbance and enzyme activity.

FIG. XXI is an elution profile of Peak IV alpha-amidating enzyme from CA-77 Cell Tissue Culture Medium by strong anion-exchange chromatography on Mono Q HR 10/10 at pH 8.0, as measured by absorbance and enzyme activity.

FIG. XXII is a schematic of steps in the cloning of the DNA sequence for Peak III alpha-amidating enzyme into plasmid vector pKK233-2 to construct the prokaryotic expression vector pAE-12.

FIG. XXIII is chromatogram of a trypsin digest of purified Peak III alpha-amidating enzyme on a Vydac C18 reverse-phase HPLC column.

DETAILED DESCRIPTION OF CERTAIN PREFERRED EMBODIMENTS

It has now been discovered that homogeneous alpha-amidating enzyme can be obtained through a multi-step procedure employing a combination of size exclusion and ion exchange chromatography from solid tumor tissue extracts, tumor cell-lines, and the tissue culture medium from such cell lines.

The enzyme has been extracted from rat medullary thyroid carcinomas ("MTCs") developed in WAG/Rij Wistar rats as described by Roos, B. A., et al., Endocrinology, 1979, Vol. 150, #1, p. 27–32. This tissue has been deposited as IVI-10028 (now ATCC 75168). The enzyme has also been extracted from other sources, notably human and rat medullary thyroid carcinoma cell lines. Rat cell line ("CA-77") was derived from rat medullary thyroid carcinoma tumors by serial passages as described by Muszynski, M. et al., JBC 1983, Vol. 258, pp. 11678–83. This cell line has been deposited as IVI-10029 (now ATCC 10919). A human cell line ("HTT 54(34)") was developed by B. A. Roos at the VA Medical Center in Cleveland, Ohio using human medullary thyroid carcinoma cells for the primary culture. The human cell line HTT 54(34) has been deposited as IVI-10031 (now ATCC CRL 10918). (See "Recognition of the Deposit of Micro-Organisms for the Purposes of Patent Procedure" evidencing these deposits and "Budapest Notification" No. 34, dated Nov. 3, 1983, the entire disclosures of which are incorporated herein by reference).

Defined tissue culture media from both the human and rat cell lines have been demonstrated to contain significant levels of alpha-amidating enzyme activity, indicating that a portion of the enzyme is secreted from the cells. The enzyme may be obtained and purified by preferably first subjecting the crude material (including spent culture media, enzyme and impurities) to anion exchange chromatography. The sample, for example, can be bulk-loaded on a preparative scale anion exchanger such as a diethyl amino ethyl ("DEAE") cartridge such as CUNO 250 available from CUNO Corp.

The alpha-amidating activity-containing composition eluted from the cartridge is then subjected to size exclusion chromatography on a resin of appropriate resolving capabilities, for example a Sephacryl S-200 superfine column which is available from Pharmacia Fine Chemicals.

The activity-containing eluant fraction is then subjected to ion exchange chromatography using a strong anion exchange matrix. A resin which may be used is the Mono Q HR5/5 strong anion exchange resin from Pharmacia Fine Chemicals and one or more passes on the column may be required for homogeneous purification of the enzyme. The Mono Q HR5/5 Column has a particle size of 10 $\mu$m, void volumes of 40% and a gel whose charged group is $CH_2$—$N^+$—$(CH_3)_3$ and whose ionic capacity is 0.28 to 0.36 mmoles/ml.

Each purification step can be monitored for both protein content and the level of alpha-amidation activity. This information is used to calculate the specific activity of the enzyme which serves as an indicator of the relative purity of the enzyme.

Peptidyl-glycine alpha-amidating monooxygenase purified in accordance with the present invention (deposited rat derived enzyme, IVI-10032 (now ATCC 75145); deposited human derived enzyme, IVI-10033 (now ATCC 75146)) has an apparent molecular mass of about 60,000 to 65,000 daltons, as determined by gel filtration.

The enzyme has been purified such that it exhibits a specific enzymatic activity of at least approximately 25 mU per mg protein and preferably at least approximately 50 mU/mg protein. Specific activity above about 150 mU per mg protein is especially preferred. Alpha-amidating enzyme has also been purified so as to exhibit a single, homogeneous, well-defined band following electrophoresis on sodium dodecyl sulfate/polyacrylamide gels (SDS-PAGE).

The purified peptidyl-glycine alpha-amidating monooxygenase is used to amidate the alpha-carboxyl group of a polypeptide having a terminal glycine residue, where the glycine functions as an amino group donor. The substrate peptide or polypeptide can be purified from natural sources, synthesized from its component amino acids, or produced by recombinant DNA techniques. The glycine-terminating polypeptide is combined with oxygen in the presence of an effective amount of the enzyme. The amount of the enzyme required depends on several variables well known to this art including particularly, but not limited to, the following: the specific activity of a given enzyme preparation, the amount and chemical nature of the substrate to be converted, the time within which conversion is to take place and the temperature and pH of the reaction mixture. Those skilled in this art will recognize other variables that may influence the precise amount of enzyme required in a given situation. The oxygen is usually present in a molar excess in the reaction relative to the substrate concentration. A desired concentration of copper ions may be provided by any copper salt whose anion does not adversely affect the reaction. With enzyme having a specific enzymatic activity of only about 1 mU/mg protein, maximum alpha-amidation occurs with a relatively high concentration of about 4 $\mu$M cupric ions. As the purity of the enzyme is increased, the concentration requirements for the exogenous cupric ion diminishes. The enzymatic activity can also be enhanced by the presence of ascorbate ions which can be provided by any ascorbic acid salt, as long as the cation of the salt does not adversely effect the reaction. For purified enzyme having a specific enzymatic activity of approximately 50 mU/mg protein, maximal activity of the alpha-amidation occurs at about 5 mM ascorbate. Alpha-amidation activity may be increased by the addition of catalase. The optimum pH for conversion of biologically relevant substrate to amidated products is between 6.5 and 7.5.

Monoclonal and polyclonal antibodies directed against the enzyme have been obtained using homogeneous enzyme as an antigen to produce an immune response in mice and chickens respectively. Both monoclonal and polyclonal antibodies have been prepared and purified by applicants as set forth in Example 8. Inventions of antibodies specific for alpha-amidating enzyme are being maintained in applicants' laboratories.

Antibodies may be immobilized on a solid matrix which is not soluble in the media in which it is to be used.

Preferably, the matrix is one resistant to degradation. The matrix is provided with a functional group capable of binding proteins wherein the functional groups are then covalently bound to antibodies. Such immobilization of antibodies will facilitate the isolation of the α-amidating enzyme from natural and/or recombinant sources. This is accomplished by mixing the immobilized antibodies with crude preparations of the enzyme. The antibodies will specifically bind the α-amidating enzyme molecules. Contaminating proteins will not bind to the antibodies and are easily removed by elution or gentle centrifugation. After removal of contaminants, the α-amidating enzyme can be removed from the immobilized antibodies by changes in ionic strength or pH, or by addition of chaotropic ions ("Affinity Chromatography: Principles and Methods, Manual, Pharmacia Fine Chemicals, Uppsala, Sweden) and recovered in a highly-purified form.

The enzyme has also been sufficiently purified to permit its amino acid sequence to be determined. This information was utilized to isolate nucliec acids coding for the enzyme.

Subsequent incorporation into an appropriate unicellular organism or host cell isolated from a multicellular organism is accomplished by standard recombinant DNA procedures, such as found in Maniatis, et al., Molecular Cloning: A Laboratory Manual, Cold Spring Harbor, 1982; or Wu, R., ed., Methods in Enzymology, Vol. 68, Academic Press, 1979, incorporated herein by reference. The resulting cells containing the heterologous DNA coding for alpha-amidating enzyme allows the production of sufficient quantities of the enzyme in order to perform in vitro post-translational alpha-amidation and theoretically permits these cells to perform this modification of a peptide or polypeptide in vivo.

Although the present invention is being described in connection with preferred embodiments thereof, many variations and modifications will become apparent to those skilled in the art. Preferred embodiments of the invention are further illustrated by the following examples.

EXAMPLE 1

Procedure for the Purification of Alpha-Amidating Enzyme Preparation from MTC Tumors Frozen rat MTC tumors were pulverized into tiny fragments and homogenized in 150 mM Tris pH 7.5, containing 250 mM sucrose, 0.25% N-acetyl glucopyranoside, 0.1 mM PMSF, 20 ug/ml pepstatin and 100 ug/ml soybean trypsin inhibitor. Typically, 25 grams of tumor tissue were homogenized in 200 ml of the above buffer on ice. Homogenization was achieved by four bursts of 20 seconds each using a Polytron homogenizer (Brinkman) at a setting of 7. The homogenate was centrifuged for 15 minutes at 9,000×g in a JA-20 rotor (Beckman) and the supernatant (Sup.1) decanted. The pellet was rehomogenized in 60 ml of the homogenization buffer for 3 bursts of 20 seconds each at a setting of 7. This second homogenate was similarly centrifuged for 15 minutes at 9,000×g. The supernatant from this centrifugation (Sup.2), was combined with Sup.1. The combined Sup.1 and Sup.2 were then centrifuged for 30 minutes at 100,000×g in an SW28 rotor (Beckman) at 4° C. To the clarified homogenate (Sup.3) sufficient ammonium sulfate crystals were added to make the solution 25 percent in ammonium sulfate. Addition of the crystals was done gradually over a 15 minute period with constant stirring of the homogenate at 4° C. After a further 30 minutes of stirring at 4° C., the mixture was centrifuged for 15 minutes at 27,000×g in a JA-20 rotor (Beckman) at 4° C. The supernatant was decanted and further ammonium sulfate was added to the supernatant to make the solution 40 percent in ammonium sulfate. After a further 30 minutes of stirring, the mixture was again centrifuged 15 minutes at 27,000×g as above. The supernatant from this centrifugation was discarded and the pellet, which contained at least 50 percent of the total enzyme activity in the homogenate, was resuspended in 50 mM Tris HCl pH 7.0 to form the Sample. The activity was 8.2 mU/mg protein.

Sephacryl S-300 Gel Filtration Size Exclusion Chromatography

Sephacryl S-300 (Pharmacia) was equilibrated in 50 mM Tris HCl pH 7.0 and poured into a K 50/100 column (Pharmacia) according to the manufacturer's instructions. The bed volume of the column was approximately 1.3 liters. The Sample was loaded onto the column in a volume representing approximately 3 percent of the bed volume of the column. Proteins were eluted from the column in 50 mM Tris HCl pH 7.0 at a flow rate of approximately 2 ml per minute. Fractiong of 10 ml were collected and assayed for alpha-amidating enzyme activity using the Dansyl-D-Tyr-Val-Gly substrate. The enzyme eluted from the column in a single peak of activity as shown in FIG. I with a molecular mass of 60,000 to 65,000 daltons. The activity was at least 50 mU/mg protein.

Mono Q Chromatography at pH 6.0—Strong Anion Exchange Chromatography

Fractions from the Sephacryl S-300 column containing the maximum enzyme activity were pooled and dialyzed against 4 liters of 20 mM bis-Tris pH 6.0 buffer. The pool was then loaded onto a Mono Q HR 5/5 column (Pharmacia) which had been pretreated according to the manufacturer's instructions and equilibrated in 20 mM bis-Tris pH 6.0. After the proteins not binding to the column were collected in the column eluant (flow through), the bound proteins were eluted with a linear salt gradient of 0 to 300 mM NaCl in 20 mM bis-Tris pH 6.0. The column was run at a flow rate of 0.5 ml per minute and fractions of 2 ml each were collected. The solution of proteins eluting from the Mono Q column at pH 6.0 was immediately neutralized by collection into tubes containing 200 ul each of 1.0M Tris pH 7.0. Fractions were assayed for alpha-amidating enzyme activity as before and a peak of activity was observed which eluted from the column at approximately 160 mM NaCl (FIG. II). The activity was 161 mU/mg protein.

Mono Q Chromatography at pH 8.0

Fractions containing the peak alpha-amidating enzyme activity from the Mono Q chromatography at pH 6.0 were dialyzed against two changes of 4 liters each of 50 mM Tris HCl pH 8.0. The enzyme was then loaded onto a Mono Q HR 5/5 column (Pharmacia) equilibrated with 50 mM Tris HCl pH 8.0. Proteins were eluted with a salt gradient of 0–300 mM NaCl in 50 mM Tris HCl pH 8.0. A flow rate of 0.5 ml per minute was used and 2 ml fractions were collected. Each fraction was neutralized by addition of 200 ul of 1.0M Tris pH 7.0 in each of the collection tubes. Two distinct peaks of enzyme activity were seen, eluting at 190 mM NaCl and 220 mM NaCl, respectively (FIG. III). The activities were at least 80 mU/mg protein and 400 mU/mg protein respectively.

Gel Electrophoresis of the Enzyme Peak Fraction from the Mono Q at pH 8.0 Chromatography An aliquot of the enzyme peak fraction eluting at 220 mM NaCl having an activity of 408 mU/mg protein was loaded onto a 10% SDS-polyacrylamide gel after heat denaturation in a buffer containing SDS and B-mercaptoethanol (FIG. IV). A single band was observed from the fraction eluting at 220 mM NaCl. The apparent molecular mass of this band is approximately 73,000–75,000 daltons.

Verification of the Identity of the 73,000–75,000 Dalton Band as the Alpha-Amidating Enzyme From additional alpha-amidating enzyme preparation purified using criteria identical to those described above, aliquots were used for electrophoresis on a non-denaturing 10% acrylamide gel. 50 ul aliquots were loaded onto each of two lanes. After electrophoresis, the protein in one of the lanes was visualized using the silver staining technique. From the second lane strips of 3 mm each were cut and each strip incubated in one well of a microtiter plate. To each well, 100 ul of a mixture containing the Dansyl substrate, catalase, ascorbic acid and 150 mM Tris pH 7.0, was added. Incubation was done for 16 hours at 37° C. with constant shaking. Aliquots from each well were then analyzed for the conversion of substrate to the amidated product. Enzymatic activity was found in two gel slices. The activity comigrated with an intensely-staining protein band in the corresponding stained gel lane (FIG. V).

EXAMPLE 2

Procedures for the Production of Recombinant Human Calcitonin

Human calcitonin is a 32-amino acid peptide hormone possessing an amidated prolyl residue at its carboxyl terminus. A microorganism was genetically engineered to produce a recombinant fusion protein which contained the amino acid sequence corresponding to human calcitonin. The fusion protein gene was designed so that the human calcitonin sequence was bracketed by an arginyl residue on its amino terminus and its carboxyl terminus by a glycyl residue which also terminated the recombinant fusion protein (see FIG. VII). Following ligation of the human calcitonin gene into a plasmid to form the appropriate fusion plasmid, a microorganism was transformed with this plasmid and expression of the fusion was obtained (see FIG. VI). This human calcitonin-containing protein was isolated from lysates of the recombinant microorganisms by precipitation. The cysteinyl residues were then converted to S-sulfonates and the lysyl residues reversibly blocked by reaction with citraconic anhydride. Since human calcitonin does not contain arginine, tryptic digestion of the recombinant fusion protein generated a peptide containing the human calcitonin sequence with a carboxyl-terminal glycine extension. This peptide was isolated by either reverse-phase HPLC (see FIG. VIII) or ion-exchange chromatography and its structure established by amino acid and microsequence analysis.

The glycyl residue of the peptide was removed and the penultimate prolyl residue converted to prolinamide by the action of the alpha-amidating enzyme preparation of this invention. An example of the conditions employed for the semi-preparative scale alpha-amidation of this peptide is as follows: The lyophilized peptide (200–300 nanomoles) (substrate) was dissolved in 200 ul of 150 mM Tris-HCl buffer, pH 7, containing approximately 750 uU of alpha-amidating enzyme preparation. The enzyme was derived from either rat MTC tissue or spent tissue culture media from the rat MTC CA-77 cell line. The enzyme was purified to an extent so that all proteolytic activity was removed. This was accomplished by a combination of ion-exchange and size-exclusion chromatography (see aforedescribed procedure). Pure, homogeneous enzyme is not a requirement. Ascorbic acid and copper sulfate were then added to this mixture in sufficient amounts to yield final concentrations of approximately 3 mM and 2 uM, respectively. The resulting solution was mixed and incubated at 37° C. for 5–6 hours. Typical conversion percentages of the substrate to product are 70–90%. Following removal of the S-sulfonate groups, the recombinant human calcitonin (rhCT) was purified by reverse-phase HPLC (see FIG. IX). The final product was characterized by its retention on reverse-phase HPLC (see FIG. X), quantitative tryptic mapping (see FIG. XI), amino acid analysis (see FIG. II), and by its biological activity (see FIG. XII). In all instances, the recombinant human calcitonin was indistinguishable from synthetic human calcitonin.

The foregoing demonstrates that the preparations of this invention are capable of amidating a physiologically relevant, substrate, e.g. human calcitonin, produced by recombinant DNA techniques, i.e. containing only "L" amino acids.

COMPARATIVE EXAMPLES

Comparison of Claimed Preparation Activity to Prior Art

Comparison of Assay Systems for Determining Specific Activity of the Claimed Preparations Several activity assay systems have been employed in the prior art. Most of the work cited as prior art has employed an assay based on the conversion of D-Try-Val-Gly to D-Tyr-Val-amide. This assay is quantitated by the use of a radiolabeled tracer ($^{125}$I-D-Tyr-Val-Gly) which is mixed with an excess of nonlabeled material (D-Tyr-Val-Gly). Measuring conversion of the labeled tracer allows extrapolation to the unlabeled material and this in turn permits a calculation of activity.

While this assay has been used by Applicants, the activity determinations of the claimed preparations are based on a direct measurement of the conversion of Dansyl-Tyr-Val-Gly to Dansyl-Tyr-Val-amide.

In order to allow a meaningful comparison of the specific activity of preparations in the prior art to that of the claimed preparations of this invention, experiments were performed to compare the assay systems.

The experimental protocols are summarized:
I. Monodansyl L-Tyr-Val-Gly

Alpha-amidating enzyme preparation isolated from rat medullary thyroid carcinoma tumors, and from tissue culture media collected from CA-77 cells was used as the enzyme source in these experiments. The concentration of enzyme used in all experiments was left constant except where noted.

The reaction mixture for the conversion of the monodansyl substrate contained:

5 $\mu$l of enzyme

5 $\mu$l of 30 mM ascorbate

5 $\mu$l of 20 uM $CuSO_4$

5 $\mu$l of 100 ug/mL bovine pancreatic catalase

5 $\mu$l containing 2 nmoles of substrate

25 $\mu$l of 150 mM TES pH 7.0

The samples were prepared in duplicate and incubated at 37° C. for 10, 20 and 30 minutes time periods. The enzymatic reaction was halted by the addition of 10 ul 500 mM EDTA. Substrate and product were separated by RP HPLC using an Hewlett Packard-1090 liquid chromatography system, and quantitation was achieved using a HP-3392 integrator. The conversion of monodansyl L-Tyr-Val-Gly to the alpha amidated product was demonstrated to be linear with respect to time.

II. $^{125}$I D-Tyr-Val-Gly

D-Tyr-Val-Gly and D-Tyr-Val-NH$_2$ were iodinated using iodobeads from Pierce Chemical Company. The radiolabeied substrate and product were used to calibrate a sulfyl-propyl cation-exchange column. $^{125}$I D-Tyr-Val-Gly was added to 650 uM D-Tyr-Val-Gly and used as the substrate. The reaction mixture for the conversion of monodansyl substrate contained:

5 µl enzyme

5 µl ascorbate (30 mM)

5 µl 100 ug/mL catalase

5 µl 20 uM CuSO$_4$

5 µl of substrate, 650 µM final conc.

25 µl of 150 mM TES pH 7.0

Samples were incubated for 10, 20, 30 minutes at 37° C. The reaction was stopped by addition of 500 mM EDTA. The entire sample was diluted with 10 mM sodium phosphate buffer pH 5.2 and applied to a sulfyl propyl cation-exchange column. Substrate does not bind to the column; the amidated product was eluted with 500 mM NaCl. The conversion of radiolabeled substrate to product was linear with respect to time.

III. D-Tyr-Val-Gly

The reaction conditions used for the amidation of D-Tyr-Val-Gly are identical to those described for the dansyl and iodinated substrates. Substrate concentration in the reaction mixture was 650 uM. Separation of substrate and product is achieved by gradient elution on RP-HPLC using a HP-1090 liquid chromatography system. The column effluents were monitored at 280 nm. The level of sensitivity for this assay is much lower than that for either dansyl or iodinated substrates. To accommodate this lower level of sensitivity, alpha-amidation reactions were performed for longer periods of time, and/or with increased amounts of alpha-amidating enzyme.

Analysis of the data for fractional conversion of $^{125}$I-D-Tyr-Val-Gly to $^{125}$I-D-Tyr-Val-amide and dansyl-Tyr-Val-Gly to dansyl-Tyr-Val-amide demonstrates that at each time point approximately 1.55 times more iodinated substrate than dansyl substrate was converted. Thus, when comparing the assay system of the prior art with the assay system used by Applicant, a conversion factor of approximately 1.5 times the activity determined by the dansyl-substrate method (Applicants') must be employed.

Furthermore, a somewhat more rigorous kinetic analysis has also been employed to compare the dansyl-Tyr-Val-Gly (Applicants') assay to the D-Tyr-Val-Gly (prior art) assay. This analysis indicates:

| Substrate | Km | Vmax |
|---|---|---|
| D-Tyr-Val-Gly (Prior Art) | 37 | 31 |
| Dansyl-Tyr-Val-Gly (Applicants') | 1.7 | 21 |

As can be seen by comparing the maximal velocity (Vmax= pmol product/min/µl) for the two substrates, the D-Tyr-Val-Gly (Prior Art) gives approximately 1.48 times as much activity as the dansyl-Tyr-Val-Gly (Applicants'). This agrees with and confirms the findings stated above.

Comparison of Activity

Eipper et al. (PNAS) discloses at page 5147, FIG. 4 a Vmax of 39 picomoles per microgram per hour. This is equivalent to a specific activity of 0.65 mU/mg protein per minute. This is the highest activity reported in any of the cited prior art. Dividing this by the aforedescribed conversion factor of 1.5, a specific activity of 0.4 mU/mg protein per minute is derived. This value can now be directly compared to the aforedescribed specific activities achieved by applicants. Applicants, as indicated previously, have achieved activities of at least 25 mU/mg protein and greater than 1500 mU/mg protein. Applicants have thus achieved activity from 60 to greater than 3,750 times Eipper's (PNAS) reported activity.

EXAMPLE 3

Purification and Characterization of Alpha-Amidating Enzymes from Rat MTC Tumor

Frozen rat MTC tissue was pulverized into tiny fragments and homogenized in an aqueous buffer using a Polytron homogenizer. After low speed centrifugation, the supernatant was saved and the pellet was reextracted with fresh buffer. This second homogenate was again subjected to low speed centrifugation, and this supernatant combined with the first one. The two pooled supernatants were then clarified by high speed centrifugation and the high speed supernatant was used as the starting material for purification of the enzyme.

Ammonium sulfate fractionation of the high speed supernatant was performed. The majority of the enzyme activity was found to precipitate in the 26–40% ammonium sulfate fraction and the pellet from this fraction was purified further as below.

Size exclusion chromatography was performed on a Sephacryl S-300 column. In Example 1 herein, all the enzyme eluted off this column in a single peak of activity. In this Example, the column length was increased and the flow rate of the column reduced. Under these new elution conditions, a major peak of activity was seen (as in Example 1) followed by a minor trailing peak that may correspond to a lower molecular weight form of the enzyme. It is unclear at this point whether the low molecular weight form of the enzyme exists in vivo, or is produced by partial proteolytic digestion during the extraction and purification procedures.

The major peak of activity from the S-300 column was pooled chromatographed on a Mono Q column at pH 6.0. A larger, preparative size column was employed in this Example than in Example 1 (the Mono Q HR 10/10), which was eluted using a less steep linear salt gradient. As a result of these changes, four peaks of alpha-amidating enzyme activity were detected at this stage, eluting at 160 mM, 200 mM, 220 mM and 240 mM NaCl. (Peaks I, II, III and IV, respectively) FIG. XIII. This indicates that there are multiple forms of the enzyme and that these forms have a charge heterogeneity. Furthermore, polyacrylamide gel analysis of the proteins in the enzyme activity peaks indicates that peaks II, III and IV contain alpha-amidating enzyme of approximately the same molecular weight (i.e. 73,000–75,000 daltons), whereas peak I had a different, probably smaller, molecular weight enzyme. The activity in peak III was purified to homogeneity as follows:

The peak III enzyme was pooled and chromatographed on a Mono Q HR 10/10 column at pH 8.0 (FIG. XIV). The enzyme eluted from this column as a single peak at 250 mM NaCl and gel analysis revealed that the enzyme was purified to homogeneity (FIG. XVa, lane 6). The following characterization experiments were performed on the peak III purified enzyme.

1. The molecular weight of the peak III enzyme was determined by 7% polyacrylamide gel analysis to be about 75,000 daltons (FIG. XVb).

2. The optimum pH for the activity of the enzyme was determined to be pH 5.0–5.5 using N dansyl Tyr-Val-Gly as the substrate (FIG. XVI). However, due to the enhanced stability of the enzyme at neutral pH, it may be beneficial to carry out the amidation reaction at such pH.

3. It was determined that the amount of copper required as a co-factor for enzyme activity was inversely proportional to the purity of the enzyme. The enzyme purified to homogeneity required 0.1 uM or less $Cu^{++}$ for maximal activity, whereas crude preparations of the enzyme require 2 uM $Cu^{++}$.

4. The iso-electric point (pI) of the enzyme was 4.8.

5. The specific activity of the homogeneous peak III enzyme was 2,100 mU/mg protein.

The peak II enzyme was also purified to homogeneity. However, with this enzyme, it was found that Mono Q chromatography at pH 8.0 was insufficient to obtain a homogeneous preparation. Therefore the pool of peak II enzyme from the Mono Q column, pH 6.0 (FIG. XIII) was dialyzed against 1M Tris pH 7.0 and loaded onto a phenyl sepharose column equilibrated with the same buffer. The majority of the contaminating protein species were recovered in the flow through of the column, and the amidating enzyme which eluted at a later stage, was substantially purified. Further purification of the pooled enzyme from the phenyl sepharose column on a Mono Q HR 10/10 pH 8.0 column resulted in a homogeneous preparation of the peak II enzyme eluting from the column at or above 220 mM NaCl.

Characterization of the peak II enzyme revealed that:

1. The molecular weight of the peak II enzyme by 7% polyacrylamide gel electrophoresis was about 73,000–75,000 daltons. Thus, the peak II and peak III enzymes were indistinguishable by comparison of their molecular mass.

2. The optimum pH for the activity of the peak II enzyme was pH 5.0–5.5. Again, this characteristic of the peak II enzyme is the same as that for the peak III enzyme.

3. The iso-electric point (pI) of the peak II enzyme was approximately 5.8.

EXAMPLE 4

Purification and Characterization of the Alpha-Amidating Enzyme Derived from CA-77 Cell Tissue Culture Media A rat medullary thyroid carcinoma cell line, CA-77, was grown as a monolayer culture in 150 $cm^2$ T-flasks (Corning) at 8%$CO_2$. The culture was maintained in defined medium consisting of Dulbecco's Modified Eagle Medium: F-10 (1:1), 3.7 g/liter of $NaHCO_3$, 5 µg/ml of transferrin, 10 µg/ml insulin, 30 nM selenium, and 4 µg/ml of gentamycin sulfate. The cultures grown in this manner could be maintained indefinitely if the medium was changed every 48 hours. To increase the stock supply of cells, they were subcultured and grown in medium containing serum (5% horse and 2.5% fetal calf serum) for three days. The cells were then washed twice with phosphate buffered saline and replenished with defined medium.

Tissue culture media was aseptically collected on a 48-hour schedule and stored at −20° C. until purified. The tissue culture media (routinely 6 liters) was diluted with 2 liters of deionized water (3:1) and applied at a flow rate of 50 ml/min to a DEAE weak anion exchange cartridge (Cuno #250) that had been previously equilibrated with 1.0 liter of 20 mM bis Tris:HCl pH 6.0 at 4° C. The alpha-amidating enzyme (alpha-AE) was eluted from the cartridge in a stepwise fashion with 50 mM Tris HCl pH 7.0 containing 500 mM NaCl at a flow rate of approximately 50 ml/min. The fractions containing alpha-AE activity (specific activity 10–15, mU/mg) from two anion exchange preparations were pooled and concentrated 4- to 5-fold under reduced pressure using the Savant RH-100 prep rotor.

This material was applied directly to a 5×50 cm column containing Sephacryl 300-SF (Pharmacia). The mobile phase was 100 mM Tris:HCl pH 7.0 with a flow rate of 1.0 ml/min. All gel filtration chromatography was also performed at 4° C. (FIG. XVII).

The amidating enzyme preparation at this stage of purification is free of nonspecific proteolytic activity and has an activity of at least 50 mU/mg protein. The amidating enzyme preparation from this step has been used successfully for the amidation of recombinant gly-extended human calcitonin and growth hormone releasing factor. Starting with a cell density of 1–1.5×$10^6$ cells/mL (from T-flasks) we have routinely obtained a yield of 200–350 mU of amidating enzyme activity/liter of spent media following these two purification steps. The enzyme is stable and appropriate for use in solution or after immobilization to a solid support.

Column fractions containing alpha-AE activity were pooled then dialyzed versus 6 liters of 20 mM bis Tris:HCl pH 6.0. The enzyme was applied to a Mono Q HR 10/10 strong anion-exchange column (Pharmacia) previously equilibrated with 20 mM bis Tris:HCl pH 6.0. The enzyme was eluted from the column using a linear gradient of 0–300 mM NaCl over a three-hour period at a flow rate of 2.5 ml/min. Four chromatographically-distinct forms of alpha-amidating enzyme activity were resolved during this purification step. The peaks were numbered in elution order from the column (FIG. XVIII). Peaks III and IV represent higher molecular weight forms of the enzyme and correspond to peaks II and III derived from MTC tumors. Peaks I and II represent lower molecular weight forms of the enzyme that may represent proteolytic fragments of peak III and IV.

The four forms of the alpha-amidating enzyme identified in our laboratory differ from each other in their net surface charge as evidenced by their differing retention times during strong anion exchange chromatography (FIG. XVIII). The pH optimum for these four chromatographically-distinct forms of the enzyme also differ. The results in FIG. XIX demonstrate that peaks III and IV have an identical pH optimum between pH 5.0 and 5.5. These results agree with the pH optimum determined for peaks II and III purified from MTC tumor. Peaks I and II have a much broader pH activity range with an optimum between pH 5 and 8.5 (FIG. XIX). These results are in close agreement to the pH optima reported by Eipper et al. *Peptides*, Vol. 4, pp. 921–28 (1983); and Murthy et al. *J. Biol. Chem.*, Vol. 261, pp. 1815–22 (1986).

Radiolabelling of enzyme from peaks II and IV with $Na^{125}I$, followed by SDS-PAGE, confirmed that the peak IV enzyme activity had an approximate molecular mass of 73–75 kDal, whereas the peak II enzyme activity was below 55 kD. The exact molecular weight is unknown for the Peak II enzyme because it was not purified to homogeneity (several protein bands are evident in the 45–55 kDal range).

Peak III and IV enzyme can be purified to homogeneity using a combination of hydrophobic interactive chromatography and strong anion-exchange chromatography at pH 8.0. Peak IV enzyme (FIG. XVIII) activity was pooled, concentrated to approximately 2 ml in vacuo and directly applied to a 1.3×8 cm column of phenyl sepharose (Pharmacia) equilibrated with 500 mM Tris:HCl pH 7.0. Fractions containing alpha-AE activity were eluted with equilibration buffer at a flow rate of 0.5 ml/min (FIG. XX). The peak fractions containing alpha-amidating activity were pooled, dialyzed versus 50 mM Tris:HCl pH 8.0, then applied to a Mono Q HR 10/10 column equilibrated with 50 mM Tris:HCl pH 8.0. The enzyme was eluted from the column using a linear gradient of 0–300 mM NaCl over a three hour period at a flow rate of 2.0 ml/min (FIG. XXI). Fractions containing alpha-AE activity eluted at or above about 240 mM were pooled, adjusted to 0.001% (v/v) in Triton X-100 and stored at 4° C. The specific activity of the purified enzyme was determined to be approximately 1500 mU/mg protein at pH 7.0. Peak III alpha-AE activity was purified to homogeneity using identical procedures to those described for peak IV.

The physicochemical characteristics of tumor peak (from Example 3) and (tissue culture peak IV (from Example 4) including molecular mass (73,000–75,000 daltons), pH optimum (5.0–5.5), amino terminal sequence, and elution position (greater than about 240 mM sodium chloride from strong anion exchange chromatography performed at pH 8.0, demonstrate that these two peaks may represent the same enzyme.

EXAMPLE 5

Alpha-Amidation of Biologically-Relevant Peptide Hormones Using the Alpha-Amidating Enzyme Several recombinant peptide hormone substrates including those for salmon and human calcitonin, human growth hormone releasing factor, and human calcitonin gene-related peptide have been produced and successfully alpha-amidated by the alpha-amidating enzyme preparation of this invention. For purposes of illustration, the procedures employed for the production of recombinant salmon calcitonin, human calcitonin gene-related peptide, and human growth hormone releasing factor are summarized below. Similar types of approaches may be used for other recombinant peptides.

Salmon calcitonin is a 32-membered peptide hormone possessing an alpha-amidated prolyl residue at its carboxyl terminus. A microorganism was genetically engineered to produce a recombinant fusion protein which contained the amino acid sequence corresponding to salmon calcitonin. The fusion protein gene was designed so that the salmon calcitonin sequence was bracketed by a methionyl residue on its amino terminus and at its carboxyl terminus by a glycyl residue which also terminated the recombinant fusion protein. Following ligation of the salmon calcitonin gene into a plasmid, a microorganism was transformed with this plasmid and expression of the fusion protein was obtained. This calcitonin-containing protein was isolated from lysates of the recombinant microorganism by precipitation and its cysteinyl residues converted to S-sulfonates. Since salmon calcitonin does not contain methionine, cyanogen bromide cleavage of the recombinant fusion protein generated a peptide containing the salmon calcitonin sequence with a carboxyl-terminal glycine extension. This peptide was isolated by either reverse-phase HPLC or ion-exchange chromatography and its structure established by amino acid composition and microsequence analysis.

The penultimate prolyl residue was converted to prolinamide by the action of the alpha-amidating enzyme. An example of the conditions employed for the alpha-amidation of this peptide is as follows: The lyophilized peptide substrate (glycine-extended salmon calcitonin precursor, 200–300 nanomoles) was dissolved in 200 uL of 150 mM Tris-HCl buffer, pH 7, containing approximately 750 uU of alpha-amidating enzyme. The enzyme can be derived from either MTC tumor or spent tissue culture media from the rat MTC CA-77 cell line. The enzyme must be purified to an extent so that all extraneous proteolytic enzyme activity has been removed. This is usually accomplished by a combination of ion-exchange and size-exclusion chromatography (see Example 4). Pure, homogeneous enzyme is not a requirement. Ascorbic acid and copper sulfate were then added to this mixture in sufficient amounts to yield final concentrations of approximately 3 mM and 2 $\mu$M, respectively. Catalase (7.5 $\mu$g/mL), ethanol (1%, v/v), and potassium iodide (50 mM) may also be incorporated into the reaction mixture to improve the yield of alpha-amidated salmon calcitonin. The resulting solution was mixed and incubated at 37° C. for 5–6 hours.

Following removal of the S-sulfonate groups with beta-mercaptoethanol treatment, the recombinant salmon calcitonin was purified by reverse-phase HPLC. The final product was characterized by its retention on reverse-phase HPLC, quantitative tryptic mapping, and amino acid analysis. In all instances, the recombinant salmon calcitonin was indistinguishable from synthetic salmon calcitonin.

Human calcitonin gene-related peptide is a 37-membered peptide hormone possessing an alpha-amidated phenylalanyl residue at its carboxyl terminus. The fusion protein gene was designed in a similar fashion to that of salmon calcitonin (see above) in that the human calcitonin gene-related peptide sequence was bracketed by a methionyl residue on its amino terminus and at its carboxyl terminus by a glycyl residue which also terminated the recombinant fusion protein. The liberation, purification, alpha-amidation, and characterization of the recombinant human calcitonin gene-related peptide precursor was also accomplished in a manner analogous to that used for recombinant salmon calcitonin.

Human growth hormone releasing factor (hGHRF) is a 44-membered peptide hormone possessing an alpha-amidated leucyl residue at its carboxyl terminus. The fusion protein gene for hGHRF was designed so that the amino acid sequence for the peptide hormone was bracketed by a tryptophanyl residue on its amino terminus and at its carboxyl terminus by a glycyl residue which also terminated the recombinant fusion protein. The hGHRF-containing fusion protein was isolated from lysates of the recombinant microorganism by precipitation. The non-hGHRF portion of the fusion protein was denatured by the conversion of the cysteinyl residues to S-sulfonate derivatives. Since hGHRF does not contain tryptophan, chemical digestion of the recombinant fusion protein with the reagent BNPS-skatole oxidatively cleaved the fusion protein, thereby generating unamidated hGHRF with a carboxyl-terminal glycine extension. Simultaneously, the methionyl residue at position 27 in the hGHRF molecule was oxidized to methionine sulfoxide. This glycine-extended peptide was isolated using gel-filtration and reverse-phase HPLC. Its structure was established by amino-acid analysis of the fragment peptides produced by trypsin digestion.

The penultimate leucyl residue was converted to leucinamide by the action of the alpha-amidating enzyme of this invention. An example of the conditions used for the preparation of alpha-amidated hGHRF is as follows: The lyophilized peptide substrate (20–40 nanomoles) was dissolved in 150 μL deionized water and mixed with 90 μL (500 μU) (pH 7.0) of alpha-amidating enzyme preparation derived from either rat MTC tumor or spent tissue culture media from the rat CA-77 cell line. The enzyme had been purified to remove all extraneous proteolytic enzyme activity by a combination of size-exclusion and ion-exchange chromatography. Ascorbic acid and copper sulfate were then added to the mixture of enzyme and substrate in sufficient amounts to yield concentrations of 3 mM and 2 uM, respectively. The resulting solution was mixed and incubated at 37° C. for 4–6 hours. A typical conversion percentage of the substrate to product is 95%, based on the amino acid analysis of the fragments liberated by digestion with trypsin. Finally, the methionine sulfoxide residue was reduced to methionine by the action of 4M beta-mercaptoethanol buffered at pH 4 with 10 mM sodium acetate at 80° C. for one hour. The final product was purified by a reverse-phase HPLC and characterized by its retention time, tryptic digestion analysis, and amino acid analysis. The recombinant, alpha-amidated product was also tested for biological activity. In all instances, the recombinant hGHRF was indistinguishable from synthetic hGHRF.

In addition to the above studies, two commercially-available glycine-extended peptide hormones were evaluated for their ability to act as substrates for the alpha-amidating enzyme. These are the precursors of alpha-melanocyte stimulating hormone and substance P. In both cases, results indicate that both peptides are suitable substrates for the alpha-amidating enzyme.

EXAMPLE 6

Sequence Analysis of Purified Rat Alpha-Amidating Enzyme

Fractions containing purified alpha-amidating enzyme were pooled from either rat MTC tumor tissue or CA-77 cell culture supernatants and the sulfhydryl groups of the enzyme were subjected to reduction followed by carboxymethylation. The resulting reaction mixtures were then applied to a Vydac C4 reverse-phase HPLC column (5 μM particle size, 33 nm pore size) that had been equilibrated with 0.1% aqueous trifluoroacetic acid. The column was washed with this solution to remove excess buffer salts. The desalted enzyme was removed from the HPLC column by eluting with 80% acetonitrile containing 0.08% trifluoroacetic acid. The column effluent was monitored by UV detection at 220 nm. The resulting protein fractions were collected, pooled, and lyophilized. This material was then redissolved in 100 μL of 0.1% SDS and then applied to an Applied Biosystems model 470A protein sequencer. Procedures used for the microsequence analysis were those specified by Applied Biosystems. The resulting phenylthiohydantoin amino acids were analyzed by HPLC on a Hypersil C18 column (Sum particle size, 10 nm pore size) with absorbance monitored at 269 and 313 nm on a Hewlett-Packard 1090 liquid chromatography system. The amino-terminal sequence of the major component enzyme peak (peak III) from the tumor tissue was as follows:

```
 1   2   3   4   5   6   7   8   9   10  11  12
NH2-Ser-Phe-Ser-Asn-Glu-Cys-Leu-Gly-Thr-Ile-Gly-Pro- 13  14  15  16  17  18  19  20  21  22  23  24  25
Val-Thr-Pro-Leu-Asp-Ala-Ser-Asp-Phe-Ala-Leu-Asp-Ile- 26  27  28
Arg-Met-Pro
```

Amino-terminal sequence data for the major component form of the enzyme (peak IV) from CA-77 cell tissue culture supernatants indicate that it is identical to that of the tumor tissue enzyme (peak III). However, a minor component was also detected during the microsequence analysis of this enzyme which appears to contain an amino-terminal extension when compared to the major form of the alpha-amidating enzyme. The presence of this component is probably due to differential post-translational processing of the enzyme. The amino-terminal amino acid sequence of this component was as follows:

```
 1   2   3   4   5   6   7   8   9   10  11  12
NH2-Phe-Lys-Glu-Thr-Thr-Arg-Ser-Phe-Ser-Asn-Glu-Cys
 13  14
Leu-Gly-
```

Additional amino acid sequence data was obtained for the α-amidating enzyme from rat MTC tumor tissue by the following procedure: Approximately 400 μg of purified enzyme was subjected to reduction and carboxymethylation. Following this procedure, the enzyme solution was transferred to dialysis tubing and dialyzed for 18 hours against 25 mM Tris-HCl pH 8.0/0.5M urea. The retentate was then transferred to a 1.5 mL centrifuge tube and concentrated to a volume of 600 μL under reduced pressure. To the enzyme solution was added 2 μL (2 μg) of trypsin and the mixture incubated for one hour at 37° C. At this point, a second aliquot of trypsin (2 μg) was added and incubation continued for two hours at 37° C. The digestion was terminated by the addition of 200 μL of 4M urea/10% acetic acid. The digest was then applied to a Vydac C18 reverse phase HPLC column (5 μm particle size, 33 nm pore size) that had been equilibrated with 0.1% aqueous trifluoroacetic acid. The column was then eluted with a linear gradient of acetonitrile to a concentration of 50% over a four-hour period and fractions collected at two-minute intervals. The resulting characteristic reverse phase HPLC elution peaks for the tryptic digest of the enzyme is graphed in FIG. XXIII. Three of the resulting tryptic peptides were subjected to automated sequence analysis as described above and the results are given below. (Peptides are designated by their fraction number.)

Tryotic Peptide No. 65
—Ser-Met-Gln-Pro-Gly-Ser-Asp-Gln-Asn-His-Phe-Ser-Gln-Pro-Thr—

Tryptic Peptide No. 58
—Asn-Gly-Gln-Trp-Thr-Leu-Ile-Gly-Arg—

Tryptic Peptide No. 86
—Phe-Val-Thr-Gln-Trp-Gly-Glu—

EXAMPLE 7

Molecular Cloning of the Gene or DNA Sequences Encoding Rat MTC or CA-77 Cell Alpha Amidating Enzyme The ability to clone the gene or DNA sequence encoding alpha-amidating enzyme derives from several critical pieces of information and reagents. One must discover a reliable source of the enzyme protein which will in turn serve as a source of the enzyme's messenger RNA (mRNA) and ultimately its complementary DNA (cDNA). Isolation of the enzyme's gene or cDNA also requires a molecular probe specific to the enzyme of interest. Generally this molecular probe takes one of two forms, it is either an oligonucleotide whose sequence is complementary to part of the enzyme gene or it is an antibody molecule (or collection of antibody molecules) that recognizes the enzyme protein specifically. Derivation of these molecular probes requires discovery of a method for purifying the enzyme such that either enzyme specific antibodies can be produced or the enzyme's amino acid sequences can be determined for designing oligonucleotide probes. These conditions of discovery have been satisfied for the alpha-amidating enzyme of this application.

The alpha-amidating enzyme was purified from rat MTC tissue and rat CA-77 cell conditioned media. This established that these cell sources would contain the mRNA encoding the enzyme protein. The methods that we have used to prepare cDNA for alpha-amidating enzyme are well known in the art of molecular biology. Specific protocols for these various methods can be found in laboratory manuals such as *Molecular Cloning* (1982), *DNA Cloning*, (Volume 1) *a Practical Approach*, (1985) or primary literature references such as Gubler J. & Hoffman, B. J., *Gene*, Vol. 25, pp. 262–269 (1983). or Young, R. A. and Davis, R. W., *PNAS*, Vol. 80, pp. 1194–98, 1983). These procedures have a general applicability with the critical variable being the source of the mRNA utilized. To prepare amidation enzyme specific cDNA we have used both rat MTC tissue mRNA and CA-77 cell mRNA. The double stranded cDNA samples that were synthesized were in turn used to prepare separate gene libraries by well known procedures.

As discussed above, identification of the particular cDNAs for alpha-amidating enzyme mRNA requires molecular probes that can distinguish these recombinants from the other recombinants in a particular library. Examples 3 and 4 detail the purification methods used to prepare the enzyme necessary for derivation of molecular probes. Example 6 describes the use of this protein to determine amino acid sequences while Example 8 describes the use of the purified protein to prepare enzyme specific antibodies.

The amino acid sequences of Example 6 are sufficient to generate specific selective oligonucleotide probes. In the preparation of oligonucleotide probes, several factors are important for making the probe selective. A full discussion of these considerations can be found in Lathe R. J., *J. Mol. Biol.*, Vol. 183, pp. 1–12 (1985). Since generally more than one nucleotide sequence can encode the same amino acid sequence (a principle known as the degeneracy of the genetic code), any single nucleotide sequence will only represent one of a number of potential gene sequences. To guarantee that an oligonucleotide probe will identify the gene of interest, one can prepare an equimolar mixture of all the possible nucleotide sequences that could encode amidation enzyme specific amino acid sequence. The complexity of such mixtures often render them less than absolutely selective and thus in general oligonucleotide mixtures corresponding to more than one region of amino acid sequence from a protein must be used to obtain absolutely specific selectivity for a given gene.

Alternatively, an oligonucleotide selective for the gene of interest can be prepared by preparing a unique nucleotide sequence of sufficient length that even slightly imperfect complementarity to the desired gene will produce a stable hybrid. This unique sequence will have a very small (length dependent) probability of forming a stable hybrid with other gene sequences. The unique sequence is comprised of the most frequently used codon for each amino acid of the protein sequence. The frequency of codon usage for a given species can be determined from a compilation of known gene sequences and the corresponding amino acid sequences for the proteins of that species. These methods are well known to those who are skilled in the art of molecular biology.

Still another approach that can be employed to prepare specific oligonucleotide probes involves the incorporation of deoxyinosine residues into the oligonucleotide at positions of maximum degeneracy. This nucleotide substitution serves to reduce the degeneracy of the probe sample and thus can have beneficial effects on the selection process. (For a discussion of the use of deoxyinosine in an oligonucleotide probe, see Ohtsuka et al., *J. Biol. Chem.*, Vol. 260, pp. 2605–08 (1985)).

We have used the alpha-amidating enzyme protein sequences to project a variety of oligonucleotide probes that are useful for amidating enzyme cDNA isolation. The sequences used and the probes we have prepared are shown in Table II. It must be recognized that if provided with the amino acid sequences, alternative strategies for gene isolation by probe hybridization could be evolved by one who is skilled as a molecular biologist.

The oligonucleotide probes so generated have been used by well established methods (see *Molecular Cloning* 1982) to screen both the plasmid and bacteriophage cDNA libraries and to isolate alpha-amidating enzyme cDNAs.

Table II

This table illustrates all of the possible gene sequences corresponding to selected regions of an alpha amidating enzyme protein. Below the projected sequences are shown some of the gene complementary oligonucleotide probes that are useful for cDNA identification and isolation.

Amino Terminus Sequence

```
AA #:              1    2    3    4    5    6    7    8    9   10   11   12   13   14   15   16   17   18
Sequence:         Ser  Phe  Ser  Asn  Glu  Cys  Leu  Gly  Thr  Ile  Gly  Pro  Val  Thr  Pro  Leu  Asp  Ala 5'
Projected         TCC  TTC  TCC  AAT  GAG  TGC  CTG  GGC  ACC  ATT  GGC  CCT  GTG  ACC  CCC  CTG  GAT  GCC
Gene              AGT   T   AGT   C    A   TTT   A    T    C    A    A    T   TTT   C    T
Sequences:         A         A                        G    A    A    G    C    T    A    A    A    G
                   G         G                   C    T    G         T    G    A    G    G    C    G 3'                                                           5'
Oligonucleotide                       TTA  CTC  ACG  GAC  CCG  TGG  TAA  CCG  GGA  CAC  TGG  GGG  GAC  CTA  CG
Probe AE1                                                                                T    G 3'                                5'
Oligonucleotide                               AC   CCG  TGG  TAA  CCG  GGA  CAC  TG
Probe AE8                                     I    I    I    I    I    I    I AA #:             19   20   21   22   23   24   25   26   27   28
Sequence:        Ser  Asp  Phe  Ala  Leu  Asp  Ile  Arg  Met  Pro Projected        TCT  GAC  TTT  GCC  CTG  GAC  ATC  CGG  ATG  CCT
Gene             AGC   T    C    T    T    T    T    A         A
Sequences:                       A    A         A    C         C
                                 G    C         T              G
```

Tryptic Peak #58

```
AA #:              1    2    3    4    5    6    7    8    9
Sequence:         Asn  Gly  Gln  Trp  Thr  Leu  Ile  Gly  Arg 5'                                        3'
Projected         AAT  GGC  CAG  TGG  ACC  CTG  ATT  GGC  CGG
Gene               C    A    A         T    T    C         A    A    A
Sequences:              G              A    T    A    G         C
                        T                   G    G              T    T 3'                   5'
Oligonucleotide   TTA  CCG  GTC  ACC  TG
Probe AE4          G    T    T 3'                   5'
Oligonucleotide   TTA  CCG  GTC  ACC  TG
Probe AE5          G    A    T
```

Tryptic Peak #65

```
AA #:              1    2    3    4    5    6    7    8    9   10   11   12   13   14   15
Sequence:         Ser  Met  Gln  Pro  Gly  Ser  Asp  Gln  Asn  His  Phe  Ser  Gln  Pro  Thr 5'                                                                      3'
Projected         TCC  ATG  CAG  CCT  GGC  TCT  GAC  CAG  AAC  CAC  TTC  TCC  CAG  CCC  ACT
Gene              AGT        A    A    A   AGC   T    A    T    T   AGT   A    T    A
Sequences:         A              C    G    A                                  A    A    C
                   G              G    T    G                                  G    G    G 3'                                      5'
Oligonucleotide        TAC  GTC  GGI  CCI  AGI  CTG  GTC  TT
Probe AE6                         T             A    T 3'                                      5'
Oligonucleotide        TAC  GTC  GGI  CCI  TCA  CTG  GTC  TT
Probe AE7                         T         G    A    T 3'                  5'
Oligonucleotide                       CTG  GTC  TTG  GTG  AA
Probe AE10                                  A         A    A 3'                  5'
Oligonucleotide                       CTG  GTT  TTG  GTG  AA
Probe AE11                                  A         A    A
```

-continued

| | Amino Terminus Sequence | | | | | | |
|---|---|---|---|---|---|---|---|
| | Tryptic Peak #86 | | | | | | |
| AA #: | 1 | 2 | 3 | 4 | 5 | 6 | 7 |
| Sequences: | Phe | Val | Thr | Gln | Trp | Gly | Glu |
| | 5' | | | | | | 3' |
| Projected | TTT | GTG | ACC | CAG | TGG | GGA | GAG |
| Gene | C | C | T | A | | T | A |
| Sequences: | | T | A | | | G | |
| | | A | G | | | C | |
| | 3' | | | | | | 5' |
| Oligonucleotide | AAA | CAC | TGC | GTC | ACC | CCC | CT |
| Probe AE9 | | G | I | I | T | | I |

EXAMPLE 8

A. Generation in Mice of Monoclonal Antibodies Specific to Alpha-Amidation Enzyme Eleven Balb/cJ mice were immunized and boosted with purified preparations of amidation enzyme. These mice were bled and the serum was processed and titered against the purified enzyme by an ELISA assay. The assay (the techniques employed are well established) was performed by absorbing the purified enzyme to a polystyrene plate which was then washed and blocked (to prevent extraneous binding of the antibodies to the plate) with bovine serum albumin (BSA). The diluted mouse sera (containing the putative antibodies against the amidating enzyme) was then incubated on the amidating enzyme-coated plate and washed. A second antibody (labeled with a marker, alkaline phosphatase, which facilitates confirmation of the binding of the first antibody to the plate-bound enzyme) was then incubated in the wells. After washing, and addition of a substrate solution, the signal was calorimetrically monitored by a spectrophotometric recorder. "Positive" sera exhibited a signal-to-noise ratio of at least 2:1.

Mouse #7, which demonstrated a high titer in the ELISA, was sacrificed four days after the final boost. The spleen was aseptically removed and teased (mechanically broken down) to yield a total of $132.6 \times 10^6$ splenocytes, which were fused to $122.8 \times 10^6$ NS-1 myeloma cells with 1.28 mls of PEG (polyethylene glycol) 4000. The cells were aliquoted into five 24-well plates which had previously been coated with Balb/cJ thymocytes and splenocytes, which served as feeder cells. The cells were maintained in selective HAT media, which permits survival of only the hybrid cells.

The supernatants from 116 wells which showed clonal growth were screened by radioimmunoassay and ELISA methods for antibody production. The radioimmunoassay procedure was similar to the ELISA previously described except that the second antibody was labeled with $^{125}I$ and the radioactive counts were measured by a gamma counter.

Fifty-six of the 116 wells were positive for antibody production and subsequently screened for reactivity to alpha-amidating enzymes. Twenty-five clones which appeared to be positive for the alpha amidating enzymes were cloned out by a serial dilution process. The primary clones were screened both against alpha-amidating enzymes and BSA (since the polystyrene plates were blocked with BSA, antibodies which were bound to the plate may have merely bound to or been absorbed by the BSA in a nonspecific manner) to determine if they were indeed specific for the amidating enzyme. Clones that demonstrated a signal for the alpha-amidating enzyme that was at least twice that demonstrated for BSA were cloned out at a 1 cell/2 well distribution ratio.

Twenty-one positive hybridomas (see Table III) were carried to the tertiary cloning stage and twenty of them characterized with regard to antibody class by both Ouchterlony and ELISA techniques. Seventeen of the clones have $IgG2a$ heavy chains and three have $IgG_1$ heavy chains. All of the twenty clones typed secrete antibodies with kappa light chains.

Each line was individually grown in bulk culture and aliquots of cells were frozen in liquid nitrogen. Pristane-primed Balb/cJ mice were injected intraperitoneally with $5 \times 10^6$ hybridoma cells. One week later, mice that did not show the onset of ascitic tumors were given a booster injection of cells. Ascites fluid and blood were removed 1–2 weeks later. After processing, the ascites and sera were screened and titered against the alpha amidating enzyme as well as against negative antigens (for example, bovine serum albumin, egg albumin, carbonic anhydrase, and growth hormone releasing factor) to ensure antibody specificity.

TABLE III

Balb/c Alpha-Amidation Enzyme Monoclonal Cell Lines

| Cell Line | Heavy Chain | Titer[1] |
|---|---|---|
| 4-1-4-20-3 | $IgG_{2a}$ | ~1:5,000 |
| 4-1-4-18-1 | $IgG_{2a}$ | |
| 4-5-7-3 | $IgG_{2a}$ | ~1:5,000 |
| 4-2-3-17-7 | $IgG_{2a}$ | |
| 3-7-1-20-24 | $IgG_{2a}$ | ~1:10,000 |
| 4-8-15-2-6 | $IgG_{2a}$ | |
| 4-7-21-14-9 | $IgG_{2a}$ | |
| 4-10-45-1-16 | $IgG_{2a}$ | |
| 54-2-1-39-2 | $IgG_{2a}$ | ~1:10,000 |
| 4-6-12-3-17 | $IgG_{2a}$ | |
| 52-1-31-24-2 | $IgG_{2a}$ | |
| 4-3-11-46-1 | $IgG_{2a}$ | |
| 3-7-9-9-3 | $IgG_{2a}$ | |
| 86-1-38-15 | $IgG_1$ | 1:1,000 |
| 4-5-6-1 | $IgG_1$ | 1:1,000 |
| 4-4-24-3-5 | $IgG_{2a}$ | ~1:5,000 |
| 4-11-3-1-8 | $IgG_1$ | |
| 8-9-94-4-2 | $IgG_{2a}$ | |
| 4-10-30-3-1 | $IgG_{2a}$ | |
| 75-10-17-14-4 | $IgG_{2a}$ | |
| 92-10-26-32-39 | Not classed | |

[1]Ascites fluids were titered with 100 ng of pure enzyme in a solid-phase ELISA.

B. Purification Procedure For Monoclonal Antibodies Produced in Mice

Monoclonal antibodies specific for the α-amidating enzyme prepared by the methods described above were purified as follows. Ascites fluid collected from several mice inoculated with the same clone was used as the antibody source. Ascites fluid was diluted (5-fold) with 10 mM MES pH 5.6. The diluted ascites fluid was applied to a 1.5×20 cm column containing 40 μm, ABX mixed-mode silica resin (J. T. Baker) previously equilibrated with 10 mM MES pH 5.6 buffer. Monoclonal antibodies were eluted from the column using a 0–500 mM sodium acetate pH 7.0 gradient. The fractions containing the purified antibodies were combined, tested for specific activity, and stored at 4° C. until futher use.

C. Generation In Chicken Of Polyclonal Antibodies Specific to α-Amidating Enzyme Intravenous, intramuscular, and subcutaneous injections were administered to two laying hens with a total of approximately 50 μg of the purified α-amidating enzyme in Ribi adjuvant for each chicken. Ribi adjuvant is a completely metabolizable lipid emulsion system which consists of a mitogen for chicken lymphocytes and an adjuvant for enhancing the antibody response to antigens in fowl (Ribi Immunochem Research, Montana). After the initial immunization, two booster injections were given at two-week intervals with approximately 30 μg of the enzyme per chicken. The animals were bled on day 21 and day 35 and the sera processed and screened for the presence of specific antibodies by the following procedure: sera from both chickens, day 0 (pre-immune), day 21, and day 35 were screened by solid-phase ELISA against 100 ng of purified α-amidation enzyme. Bovine serum albumin was used as a negative control for nonspecific antibody binding. The enzyme-specific antibodies were detected with rabbit anti-chicken IgG alkaline phosphatase-labeled sera.

The results from the above procedures demonstrated that specific antibodies could be detected in the sera of chicken 257 at day 35. Serum diluted 1:10,000 gave a signal-to-noise ratio of approximately 4:1. Chicken 258 showed enzyme-specific antibodies at day 21 and day 35. From both bleeds, sera diluted 1:10,000 gave a signal-to-noise ratio of approximately 4:1. Collection of eggs from both hens started on day 56. IgY's isolated by polyethylene glycol (PEG) precipitation of pre-immune eggs and post-immunization eggs were analyzed by Ouchterlony techniques and enzyme-specific antibodies were screened by ELISA.

D. Purification of Chicken IgY Antibodies

Polyclonal avian antibodies specific for the α-amidating enzyme were produced in chickens as described above. Eggs from immunized hens were collected and either embedded in paraffin or frozen until use for the purification of IgY. Egg whites were separated from the yolks, which contain the α-AE specific antibodies. Egg yolks were diluted 3-fold using 10 mM sodium phosphate pH 7.5 containing 0.1M NaCl and 0.01% sodium azide. An initial PEG precipitation step was performed using a 3.5% final concentration of PEG 8000. The precipitate was allowed to form for 30 minutes at room temperature, then centrifuged, and the supernatant (containing the IgY) saved. Additional PEG was added to the supernatant to bring the final concentration to 12.5% PEG. The IgY antibodies precipitated at this concentration of PEG and were pelleted by centrifugation. The IgY antibodies at this stage of the purification were purified further by two methods:

1) The precipitated IgY antibodies were resuspended in 10 mM MES pH 5.6, then dialyzed overnight at 4° C. against this same buffer. The sample was then applied to 1.5×20 cm column containing 40 μm, mixed-mode ABX silica resin (J. T. Baker). The subsequent purification protocol was identical to that described for ascites fluid.

2) Alternatively, the pellet containing IgY was resuspended in starting buffer and then reprecipitated using saturated ammonium sulfate (3:1 v/v). The pellet containing IgY was resuspended in a small volume of distilled H$_2$O and stored at 4° C. until further use. The immobilization procedure for chicken IgY is described in Example 12.

EXAMPLE 9

Kinetic Studies of Alpha-Amidating Enzyme Activity

The alpha-amidation enzyme which we have purified to homogeneity (both from medullary thyroid carcinoma CA-77 cells in culture, and from the corresponding tumor tissue removed from laboratory rats) functions in the conversion of inactive glycine-extended peptide prohormones to the bioactive C-terminal amides. Based upon our studies, the C-terminal amino acid of the prohormones must be a glycine residue in order for the enzyme to recognize it and amidate it as follows:

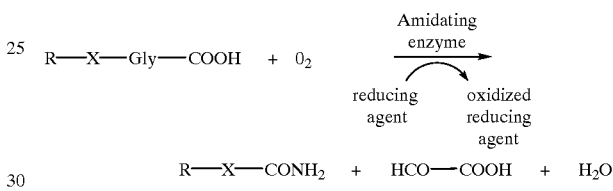

In vitro reconstitution of this activity absolutely requires in addition to the peptide substrate, molecular oxygen, and a reducing agent (L-ascorbic acid). We have found however that enzymatic activity may be substantially increased by the addition of $Cu^{+2}$ ions (copper sulfate) and catalase. This exogenous copper is bound by the enzyme and used as a site of molecular oxygen binding and activation. On the other hand, catalase is an enzyme that serves to scavenge the hydrogen peroxide which would otherwise accumulate, through side reactions involving oxygen, ascorbate, copper, and destroy the amidating enzyme.

We have successfully developed sensitive non-radiometric assay procedures for the detection of alpha-amidating enzyme activity. These assays incorporate the use of synthetic tripeptide substrates. Amidation of these substrates is conveniently monitored by separation and quantification of the product (amidated dipeptide and substrate tripeptide) using HPLC. The most sensitive of the assays developed utilizes monodansyl L-Tyr-Val-Gly as substrate. This compound can be detected at extremely low levels because the dansyl group is fluorescent. Consequently, the sensitivity of this assay is comparable to that of similar radiometric assays developed in other laboratories.

We have used this assay to investigate the kinetic properties of the alpha-amidating enzyme. In particular, the kinetic parameters Km and Vmax have been determined by examination of the effect of variation of substrate concentration upon enzymatic activity. Km is a measure of the affinity that the enzyme possesses for a particular substrate. The smaller the Km the greater the affinity. Vmax is the maximum velocity at which the enzyme will convert the substrate to product and is observed at saturating concentrations of substrate (i.e., the substrate is present in large excess over the enzyme).

In a typical amidation enzyme assay, the reation system (50 ul) would comprise enzyme (approximately 7 µg), dansyl L-Tyr-Val-Gly (up to 40 µM), L-ascorbic acid (3 mM), catalase (0 to 100 µg ml$^{-1}$), and copper sulfate (0 to 2 uM) in 60 mM TES buffer at pH 7.0. The reaction is initiated at 37° C. by the addition of enzyme and terminated after a defined period of time by the addition of 0.1 M EDTA (final concentration), which binds up copper making it unavailable for the enzyme.

The alpha-amidating enzyme displays a high affinity for the enzymatic amidation of dansyl L-Tyr-Val-Gly with the Km ranging between 1–2 µM. This value seems to be constant regardless of the state of purification of the enzyme. Thus, the enzyme pool derived from Sephacryl S-300 chromatography displays the same Km as the electrophoretically pure preparations of enzyme derived from Mono Q pH 8.0 chromatography or the lower molecular weight forms resolved on Mono Q pH 6.0 chromatography. On the other hand, as expected, the Vmax values (expressed per mg of protein) vary substantially with the state of purification. Thus, while the Vmax of the Sephacryl S-300 derived pool is approximately 50 to 100 nmol product formed per minute per mg protein, the Vmax for the pure tumor enzyme is about 5000 nmol product formed per mg protein.

We have found that the ascorbate and the substrate may compete with each other for the enzyme under some conditions. For example, if the concentration of substrate is increased substantially beyond the saturating level, enzyme activity is attenuated due to impaired interaction between enzyme and ascorbic acid. Thus for each particular substrate there appears to be a fine balance between optimal substrate/ascorbate levels, depending upon the affinity of the enzyme for the particular substrate.

Affinity of the Amidating Enzyme for Glycine-Extended Peptides

We have used the assay of monodansyl L-Tyr-Val-Gly amidation as a sensitive probe for the reaction between the amidation enzyme and several gly-extended peptide prohormones. The purpose of this study was to examine the relative affinity of the enzyme for binding certain different types of peptide substrates. Although we have shown earlier that the enzyme successfully amidates the glycine-extended precursor substrates of human calcitonin and human growth hormone releasing factor, this says nothing about the ability of the enzyme to preferentially bind these or other peptides relative to one another.

We have shown that glycine-extended alpha-melanocyte stimulating hormone, substance P, vasopressin analogs, and growth hormone releasing factor will interact with high affinity with the amidating enzyme, preventing it from metabolizing dansyl L-Tyr-Val-Gly. Furthermore, pentapeptide models corresponding to the five C-terminal amino acids residues of glycine-extended human calcitonin, neuropeptide Y, cholecystokinin, corticotrophin releasing factor and calcitonin gene-related peptide, show competition in this assay. In other words, the enzyme has the ability to bind and presumably to amidate all of these glycine-extended peptide substrates.

In contrast, when the amidated peptides corresponding to these substrates were examined, they were found to be much less able to interact with the enzyme. The capacity of this enzyme catalytic site to recognize a wide variety of glycine-extended substrates should make it an extremely useful general reagent for the commercial amidation of peptide prohormones generated by recombinant DNA technology.

EXAMPLE 10

ISOLATION OF A DNA SEQUENCE ENCODING PEAK III α-AMIDATING ENZYME

RNA Preparation:

Total RNA was prepared from rat MTC tissue using the guanidine thiocyanate procedure. Poly A RNA was selected with oligo dT cellulose.

cDNA Synthesis:

Double stranded cDNA was prepared by well known methods. Using poly A RNA from the rat MTC tissue as template and oligo dT$_{12-18}$ as a primer, first strand synthesis was accomplished in an enzymatic reaction with reverse transcriptase. The cDNA and the RNA were separated and the RNA degraded with alkali. Second strand synthesis of the cDNA was self-primed using E. coli DNA polymerase I. S1 nuclease digestion was employed to remove hairpin loops in the cDNA and to degrade any single stranded regions of the cDNA. After a reaction with DNA polymerase I to generate flush ends on the cDNA, the double stranded cDNA was treated with EcoR1 methylase and s-adenosyl methionine to methylate the EcoR1 sites and protect them from subsequent enzymatic cleavage. EcoR1 linkers were ligated to the cDNA. Following EcoR1 digestion, the excess linkers were separated from the cDNA and the cDNA was size fractionated on a Sepharose 4B column. For one such synthesis, molecules of greater than 500 base pairs were collected while in a second, molecules larger than 1000 base pairs were pooled for cloning.

λ gt11 cDNA Library Construction:

Following the synthesis of linker adapted double-stranded cDNA, the molecules were used to generate cDNA libraries in the vector λgt 11. This was accomplished by ligation of the cDNA to λgt 11 DNA that had been cleaved with EcoR1 and treated with phosphatase to prevent self-ligation of the vector DNA. Following the ligation of the DNAs, the recombinant DNAs were packaged in vitro to form infectious bacteriophage particles. (Extracts for packaging are commercially available from Promega Biotech or Clontech Laboratories or can be prepared according to standard methods.)

After the DNA was packaged, aliquots of the packaging mixture were tested to determine the number of recombinants in the libraries. One of the libraries was found to contain about 2.57×10$^6$ infectious particles, approximately 78% of which were apparent recombinants (giving clear plaques on X-Gal plates when grown in the presence of IPTG). The other library was found to have about 2.75×10$^6$ total plaque forming units and approximately 81% apparent recombinants.

Library Screening:

In order to identify which recombinant bacteriophage contained cDNA to alpha amidating enzyme protein, the phage were screened with radiolabelled oligonucleotide probes designed from the specific amino acid sequences of the alpha amidating enzyme. (See Example 7, Table II). Screening was accomplished by plating samples of bacteriophage and lifting copies of the phage onto nitrocellulose filter disks. Procedures for phage immobilization on nitrocellulose filters are widely known. Duplicate filters from each plate were hybridized with $^{32}$P-labelled oligonucleotide AE 9. Hybridization was performed at 37° C. for 20–24 hours in 6×NET, 0.5% NP40, 5×Denhardt's solution, 100 ug/ml salmon sperm DNA, with oligonucleotide probe at 0.3–0.4 pmols/ml. Following hybridization, the filters were washed in 6×SCC at 44–45° C. for several hours and exposed to X-ray film. Positively hybridizing phage were identified as coincident spots on duplicate filters. These were purified by serially enriching through several rounds of plating and hybridization. From about 4–5×10⁴ phage screened, 18 were identified by AE 9.

To confer specificity on the selection, hybridization with a second alpha amidating enzyme oligonucleotide, AE 8, was performed. This probing revealed that at least four of the eighteen phage were carrying cDNA to the alpha amidating enzyme protein sequences. This finding was confirmed by additional specific oligonucleotide hybridization (with AE 4 and AE 5) as well as by DNA sequence analysis.

α-Amidating Enzyme Expression:

The peak III αAE for which we have determined protein sequences has a molecular weight of about 75,000 daltons. If the average molecular weight of an amino acid is taken as 120 daltons, then the amidating enzyme has, at most, 625 amino acids. The gene for 625 amino acids must contain at least 1875 base pairs. All of the four cDNAs that we have isolated as amidating enzyme specific are sufficiently large to completely code for the α-amidating enzyme protein. One of the cDNA clones, λAE1, is approximately 2,200 nucleotides in length. Within the first 50 nucleotides from one end, it begins coding for the amino acid sequences that have been identified as the amino terminus of the Peak III enzyme. It can therefore be inferred that this cDNA contains the entire coding capacity necessary for Peak III enzyme. Given this information and the nucleotide sequences at the ends of the 2,200 bp cDNA, it is a relatively straightforward procedure to adapt the cDNA for expression cloning into a prokaryotic host such as E. coli.

One potential procedure that can be applied to the λAE1 cDNA is outlined in FIG. XXXII. For instance, the 2,200 base pair insert cDNA of λAE1 is isolated following EcoR1 digestion of the recombinant bacteriophage DNA and agarose gel electrophoresis. It is cloned into the EcoR1 site of pBR322 to generate the plasmid pAE8-1. pAE8-1 contains a unique KpnI cleavage site within the cDNA sequences and a unique Hind III site within the pBR 322 sequences. Digestion of pAE8-1 with KpnI and Hind III yields a fragment of about 2.15 Kb which has lost about 62 base pairs of cDNA (at the amino terminal coding end of the cDNA). To build back the amino acids found at the amino terminus of the Peak III amidating enzyme and to adapt the cDNA for cloning into an expression plasmid, the KpnI-Hind III ended fragment is ligated to oligonucleotide linker adapters. In the example shown, the E. coli expression plasmid pKK233-2 purchased from Pharmacia is being used. The 2.15 Kb cDNA fragment is ligated to the double stranded linker-adapter comprised of AE17(+)30⁵'CATGTCATTTTCCAATGAATGCCTTG-GTAC³'and

AE18(-)22⁵'CAAGGCATTCATTGGAAAATGA³'.

The adapted fragment is then ligated to the plasmid pKK233-2 DNA that has been previously cleaved with NcoI and Hind III to yield a 4.6 kb linear vector. The ligated product, pAE12, contains the cDNA for the alpha amidating enzyme preceeded by an ATG start codon and a ribosome binding site and under the control of the hybrid, IPTG inducible promotor, trc. The gene is followed by 5S RNA gene and transcription termination site. IPTG inducible expression of pAE12 is obtained following transformation of the plasmid DNA into an E. coli strain with a laciq genotype.

Partial DNA Sequence of the 2.2 kb cDNA Insert of λAE1.

The 2.2 kb insert was excised by EcoR1 digestion of λAE1, and the insert was labeled with ³²p - - - . After a secondary digestion with Hinc II, the resulting 1.6 kb and 0.6 kb fragments were sequenced by the chemical degradation method of Maxam and Gilbert.

DNA Sequence Obtained by Maxam-Gilbert Sequencing of 600 bp Fragment of λAE-1 From the Eco R1 End:

```
               v         v         v         v         50v
     AATTCCGGTCTTTAAGAGGTTTAAAGAAACTACCAGATCATTTTCCAATG v         v         v         v         100v
     AATGCCTTGGTACCATTGGACCAGTCACCCCTCTTGATGCATCAGATTTT v         v         v         v         150v
     GCGCTGGATATTCGCATGCCTGGGGTTACACCTAAAGAGTCTGACACATA v         v         v         v         200v
     CTTTCTGCACGTCCATGCGTCTACCT
```

DNA Sequence Obtained by Maxam-Gilbert Sequencing of the 1600 bp Fragment of λAE-1 From the Eco R1 End:

```
               v         v         v         v         50v
     AATTCCGTCTCAGTTTCTGTTTCTCTTGCATCTTCTGCAATTCTGAGGAG v         v         v         v         100v
     GTGGGTTTGTTCTCCACTTTGGGTTCGACAACTGCCTCGGCTTCTTTGAT v         v         v         v         150v
     TTCGTGGACTTCGATGCCAGCCTTTTTAACTGACGCATGCTCCATTTTTT v         v         v         v         200v
     CGGTCAGGGTGAACTTCCACACGGTGTTGTGTGTGCGCTCGAAGACCG
```

Search For Sequence Homology To The Oligonucleotide Probe AE8(−)22

A computer search was carried out for the homology between the amino acids used to generate the probe AE8 (Leu-Gly-Thr-Ile-Gly-Pro-Val-Thr) and the translation of the partial DNA sequence of the 600 bp fragment of λAE1.

A region of perfect homology was obtained and this region has been highlighted by asterisks on the DNA sequence and upper case letters for the amino acids. The amino acids identified by NH₂-terminal sequencing of the purified amidating enzyme have been bracketed. Amino acid assignments that are found to differ from those predicted by the DNA sequence are indicated by a "+".

```
AATTCCGGTCTTTAAGAGGTTTAAAGAAACTACCAGATCATTTTCCAATG
----.----+----.----+----.----+----.----+----.----+  50
   i  p  v  f  k  r  f  k  e  t  t   r (s  f  s  n  e
                                         +

********************
AATGCCTTGGTACCATTGGACCAGTCACCCCTCTTGATGCATCAGATTTT
----.----+----.----+----.----+----.----+----.----+  100
   c  L  G  T  I  G  P  V  T  p  l  d  a  s  d  f
                                  +           +
```

-continued

```
GCGCTGGATATTCGCATGCCTGGGGTTACACCTAAAGAGTCTGACACATA
----.----+----.----+----.----+----.----+----.----+    150
  a  l  d  i  r  m  p)  g  v  t  p  k  e  s  d  t  y
                                                      +
CTTTCTGCACGTCCATGCGTCTACCT
----.----+----.----+----.-                            176
  f  l  h  v  h  a  s  t  .
```

EXAMPLE 11

Enzyme Immobilization

Purification of α-AE:

Prior to immobilization α-amidating enzyme was purified via weak-anion-exchange and gel filtration chromatography (Example 4). In some cases the enzyme preparation may be further purified using either immunoaffinity chromatography or phenyl sepharose chromatography. The subsequent immobilization procedure is independent of the purification procedure; routinely however, the specific activity should be at least 25 mU and preferably 50 mU or higher.

Immobilization of α-AE:

The immobilization technology for the α-amidating enzyme may be based upon the simultaneous reaction of three components, the enzyme, a water soluble copolymer of acrylamide (PAN) and a low molecular weight cross-linking reagent (TET). The preformed polymer (PAN) consists of acrylamide and N-acryloxysuccinimide which is polymerized in THF solution using thermal initiation with azobis (isobutyronitrile). The cross-linking reagent may be α,ω-diamine, triethylenetetramine, (TET) cystamine. The reaction of the diamine with the active ester groups of PAN crosslinks the polymer chains via an amide linkage and forms an insoluble gel. The amino functions of the enzyme (preferably the ε-amino group of lysine) at the same time react with residual active esters on the gel and form stable covalent amide linkages. The immobilization procedure is performed in the presence of substrate and cofaotors. The presence of a high affinity substrate and oofaotors at concentrations greater than $K_m$ inhibit reactions between PAN active esters and nuoleophilic groups at or near the catalytic site of the enzyme thus protecting the enzyme from chemical inactivation.

Immobilization Conditions:

Partially purified α-AE is solubilized in 30 mM HEPES buffer pH 7.0. The ratio of PAN and TET are established such that 15% of the active esters are left unreacted which serve as the binding sites for the α-amidating enzyme. The standard PAN solution is 20% (w/w). The α-amidating enzyme reaction mixture consists of 0.2 μM $CuSO_4$, 40 μM dansyl His-Phe-Gly and 10 mM ascorbate and 0.5–2.0 mg α-AE/gram PAN. The TET concentration is calculated to equal 0.85 equivalents of primary amine/equivalent of active ester. Routinely to determine optimum conditions, a reaction without enzyme is run to establish gel time, that is the duration of time following addition of TET required to attain gel formation. The optimum yields for immobilization of α-amidating enzyme are obtained when addition of the enzyme is moved closer to the gel point. The general rule is the shorter the time the enzyme is exposed to PAN before gel formation the higher the yield of active immobilized enzyme. For most reactions α-AE (~2.0 mg/gram of PAN) is added 45–60 seconds after TET. The enzyme-containing gel is allowed to stand at room temperature for approximately one hour to allow the coupling reaction to go to completion. Following 60 minutes the gel is ground with a mortar and pestle yielding fragments averaging 100μ in size. These particles are washed with ammonium sulfate to remove unbound reactants and to convert residual active ester groups to amides thereby capping the reactive groups. The yield of active α-amidating enzyme following immobilization is expected to be less than 60%. The washes following immobilization may contain 30 to 40% of the starting activity. The α-amidating enzyme can be recovered from the washes by increasing the ammonium sulfate concentration to 45% which results in precipitation of active α-amidating enzyme.

The immobilized gel particles are appropriate for batch α-amidation reaction where particles are kept in suspension with a mechanical stirrer. After the enzymatic reaction is complete the particles are allowed to settle and the supernatant containing the amidated peptide product is decanted. This procedure is not optimal for larger scale reactions. The enzyme containing gel particles are not rigid enough to pack into a column and obtain reasonable flow rates. To circumvent this problem two alternative approaches are possible:

1. The gel is allowed to polymerize in the presence of glass beads; typically, one minute before gel point, glass beads are added to the reaction mixture and stirred with a mechanical stirrer until the beads are covered with a layer of PAN solution. The flow characteristics of this composite material are much better than those of the gel particles alone.

2. Alternatively the PAN particles are mixed with the filtration aid Celite 545. Typically a mixture of PAN and Celite is prepared with PAN constituting less than 8% w/w (dry weight) of the mixture. To generate this type of column the gel particles are suspended in 50 mM Tris:HCl pH 7.0 and with constant stirring the Celite 545 is added and allowed to mix for two hours. A column is packed with this slurry (3×40 cm) and the column temperature maintained at 37° C. to facilitate the amidation reaction. Using this approach a flow rate of 8–10 liters/day is maintained.

An attractive alternative to column chromatography is the use of a tangential flow system. The PAN polymer prior to gel point is poured over a sheet of polysulfone 0.45 μm pore support. Following gel formation the sheets can be cut to fit Millipore or New Brunswick tangential flow ultra filtration units. In this design the composite sheets of polysulfone-PAN immobilized enzyme gel are stacked in layers yielding a tremendous increase in surface area. This approach can be directly scaled up to flow rates approaching liters per minute. This type of system also provides a convenient method of recycling the reaction mixture to maximize the amidation of the peptide substrate.

The advantages afforded by immobilizing the α-amidating enzyme include recovery and reuse of the enzyme. Secondly, the immobilized matrix increases enzyme stability and provides a working form of the enzyme capable of large scale amidation reactions (gram to kg quantities of substrate) over extended periods of time.

EXAMPLE 12

Preparation of Immunioffinity Column for Purification of Impure Alpha-Amidating Enzyme Compositions A. Immobilization Procedure:

The immobilization matrix used was cyanogen bromide-activated Sepharose 4B (Pharmacia). The dry gel was first washed with 1 mM HCl (200 ml/gram resin) to swell and wash the solid support. Approximately 40 mg of purified polyclonal antibody purified from chicken egg yolks was dialyzed against 100 mM NaHCO$_3$ pH 8.3 containing 0.5M NaCl. Coupling was performed using 8 ml of the previously swollen and washed solid support. The reaction was performed for three hours at room temperature in 100 mM sodium bicarbonate buffer pH 8.3 containing 500 mM NaCl which was included to reduce nonspecific binding of protein to the solid support. The remaining active groups of the gel were blocked using 0.2M glycine. Following the blocking step the gel was washed four to five times using a cycle of high and low pH buffers (high pH buffer 100 mM NaHCO$_3$ pH 8.3+500 mM NaCl, low pH buffer 100 mM acetate pH 4.0+500 mM NaCl). These washing steps removed any unbound protein and blocking reagent (glycine) from the resin. The immunoaffinity resin was stored at 4° C. in a basic pH buffer containing merthiolate as a bacteriostatic agent. All subsequent immunoaffinity chromatography is performed at 4° C. A similar method can be used to immobilize purified monoclonal antibodies.

B. Immunoaffinity Chromatography:

The immunoaffinity column is used as an alternative high efficiency step in the purification of a-AE. Tissue culture media from CA-77 cells (see Example 4) is diluted with distilled water and pumped through a DEAE anion-exchange cartridge previously equilibrated with 20 mM Bis Tris-HCl pH 6.0. The α-amidating enzyme is eluted from the cartridge with 50 mM Tris:HCl pH 7.0 containing 500 mM NaCl. The fractions containing α-AE activity are either dialyzed vs. Tris:HCl pH 7.0 buffer or purified further using gel filtration chromatography (Example 4) prior to immunoaffinity chromatography. Samples containing α-AE are passed over the immunoadsorption column at neutral pH. The antibodies will specifically bind α-amidating enzyme while contaminating proteins will not be bound and are removed in the eluant. The α-AE activity may be eluted from the column using 100 mM glycine:HCl buffer pH 3.0, (other desorption agents including urea, dioxane, ethylene glycol, and NaI may be used). The fractions are collected into 1.0M Tris:HCl pH 7.0 to neutralize the buffer system thereby preserving α-AE activity.

What is claimed is:

1. An enzymatic composition comprising a rat alpha-amidating enzyme capable of catalyzing the conversion of a peptidyl substrate to a peptidyl amide, said peptidyl amide having an amino group in place of a C-terminal amino acid of said substrate, said enzymatic composition being sufficiently pure in alpha-amidating enzymes to exhibit a specific activity of at least about 25 mU per mg of protein present in said enzymatic composition, and said enzymatic composition being sufficiently free of proteolytic impurities to be suitable for use with substrates purified from natural sources or produced by recombinant DNA techniques.

2. The enzymatic composition according to claim 1, wherein said composition contains at least one alpha-amidating enzyme from a source selected from the group consisting of medullary thyroid carcinoma tumors, cell lines of medullary thyroid carcinoma, and tissue culture media from said cell lines.

3. The composition of claim 1, wherein said specific activity is at least about 50 mU per mg of protein present.

4. The composition of claim 1, wherein said alpha-amidating enzyme is present at a purity sufficient to exhibit a single homogeneous band on SDS-PAGE.

5. A method for purifying a rat alpha-amidating enzyme capable of catalyzing the conversion of a peptidyl substrate to a peptidyl amide, said peptidyl amide having an amino group in place of a C-terminal amino acid of said substrate, said method comprising the steps of subjecting a composition containing said alpha-amidating enzyme to size exclusion chromatography and to strong anion exchange chromatography.

6. The method of claim 5, wherein a source of said alpha-amidating enzyme is selected from the group consisting of medullary thyroid carcinoma tumors, cell lines of medullary thyroid carcinoma and tissue culture media from said cell lines.

7. The method of claim 5, wherein strong anion exchange chromatography is performed subsequent to size exclusion chromatography and is performed upon a portion of the eluant of size exclusion chromatography which displays activity characteristic of said alpha-amidating enzyme.

8. The method of claim 7, further comprising an additional anion exchange chromatography step prior to said size exclusion chromatography step.

9. A method for producing a rat alpha-amidated product comprising reacting a peptidyl substrate in the presence of an enzymatically effective amount of an enzymatic composition comprising an alpha-amidating enzyme, said enzymatic composition being sufficiently pure in alpha-amidating enzymes to exhibit a specific activity of at least about 25 mU per mg of protein present in said enzymatic composition and said enzymatic composition being sufficiently free of proteolytic impurities to be suitable for use with substrates purified from natural sources or produced by recombinant DNA techniques.

10. The method of claim 9, wherein said enzymatic composition contains at least one alpha-amidating enzyme from a source selected from the group consisting of medullary thyroid carcinoma tumors, cell lines of medullary thyroid carcinoma, and tissue culture media from said cell lines.

11. The method of claim 9, wherein said specific activity is at least about 50 mU per mg of protein present.

12. The method of claim 9, wherein said alpha-amidating enzyme is present at a purity sufficient to exhibit a single homogeneous band on SDS-PAGE.

13. The method of claim 9, wherein said substrate is contacted with said enzymatic composition in the presence of at least one substance selected from the group consisting of cupric ions, molecular oxygen and a reducing agent.

14. The method of claim 9, wherein said substrate is contacted with said enzymatic composition in the presence of a reaction-enhancing concentration of catalase.

15. The method of claim 9, wherein said substrate is contacted with said enzymatic composition in the presence of a reducing agent.

16. The method of claim 9, wherein said enzymatic composition comprises peptidyl glycine alpha-amidating mono-oxygenase, and wherein said substrate includes a glycine residue at the C-terminus of a peptide chain.

17. The method of claim 9, wherein said substrate is selected from the group consisting of naturally occurring peptides, substrates produced by a recombinant DNA technique and substrates produced by in vitro synthesis of component amino acids.

18. The method of claim 9, wherein said substrate is a calcitonin.

19. The method of claim 15, wherein said reducing agent comprises ascorbate.

* * * * *